US009028807B2

(12) United States Patent
Dickerson et al.

(10) Patent No.: US 9,028,807 B2
(45) Date of Patent: May 12, 2015

(54) SYNTHESIS MODELS FOR ANTIMICROBIAL AGENTS VIA THE HALOGENATION OF ORGANIC/INORGANIC COMPOSITES

(71) Applicant: UES, Inc., Dayton, OH (US)

(72) Inventors: Matthew B. Dickerson, Beavercreek, OH (US); Rajesh R. Naik, Centerville, OH (US)

(73) Assignee: UES, Inc., Dayton, OH (US)

( * ) Notice: Subject to any disclaimer, the term of this patent is extended or adjusted under 35 U.S.C. 154(b) by 0 days.

(21) Appl. No.: 13/803,448

(22) Filed: Mar. 14, 2013

(65) Prior Publication Data

US 2014/0050691 A1    Feb. 20, 2014

Related U.S. Application Data

(60) Provisional application No. 61/620,731, filed on Apr. 5, 2012.

(51) Int. Cl.
| | |
|---|---|
| A01N 59/00 | (2006.01) |
| A01N 33/04 | (2006.01) |
| A01N 37/18 | (2006.01) |

(52) U.S. Cl.
CPC ............... *A01N 59/00* (2013.01); *A01N 37/18* (2013.01); *A01N 33/04* (2013.01)

(58) Field of Classification Search
None
See application file for complete search history.

(56) References Cited

U.S. PATENT DOCUMENTS

| | | | |
|---|---|---|---|
| 4,681,948 A | 7/1987 | Worley | |
| 4,874,532 A | 10/1989 | Worley | |
| 5,057,612 A | 10/1991 | Worley et al. | |
| 5,490,983 A | 2/1996 | Worley et al. | |
| 5,670,646 A | 9/1997 | Worley et al. | |
| 5,808,089 A | 9/1998 | Worley et al. | |
| 5,882,357 A | 3/1999 | Sun et al. | |
| 5,889,130 A | 3/1999 | Worley et al. | |
| 5,902,818 A | 5/1999 | Worley et al. | |
| 6,077,319 A | 6/2000 | Sun et al. | |
| 6,087,294 A | 7/2000 | Klabunde et al. | |
| 6,162,452 A | 12/2000 | Worley et al. | |
| 6,294,185 B1 | 9/2001 | Worley et al. | |
| 6,417,423 B1 | 7/2002 | Koper et al. | |
| 6,469,177 B1 | 10/2002 | Worley et al. | |
| 6,548,054 B2 | 4/2003 | Worley et al. | |
| 6,768,009 B1 | 7/2004 | Sun et al. | |
| 6,770,287 B1 | 8/2004 | Sun et al. | |
| 6,809,205 B1 * | 10/2004 | Elnagar et al. | 548/320.5 |
| 6,852,312 B2 | 2/2005 | Worley et al. | |
| 6,969,769 B2 | 11/2005 | Worley et al. | |
| 7,335,373 B2 * | 2/2008 | Worley et al. | 424/405 |
| 7,335,808 B2 | 2/2008 | Koper et al. | |
| 7,507,670 B2 | 3/2009 | Shih et al. | |
| 7,541,398 B2 | 6/2009 | Sun et al. | |
| 7,687,072 B2 | 3/2010 | Worley et al. | |
| 7,713,927 B2 | 5/2010 | He et al. | |
| 7,893,109 B2 | 2/2011 | Bassiri et al. | |
| 8,211,361 B2 | 7/2012 | Sun et al. | |
| 8,278,482 B2 | 10/2012 | Jain et al. | |
| 8,329,638 B2 * | 12/2012 | Otto et al. | 514/1.1 |
| 8,367,823 B2 | 2/2013 | Sun et al. | |
| 2005/0095690 A1 * | 5/2005 | Naik et al. | 435/168 |

FOREIGN PATENT DOCUMENTS

WO    2009096993 A1    8/2009

OTHER PUBLICATIONS

Dickerson, M. et al.; Unlocking the Latent Antimicrobial Potential of Biomimetically Synthesized Inorganic Materials; Advanced Functional Materials; 2013; pp. 1-10; Wiley-VCH Verlag GmbH & Co KGaA, Weinheim.
Worley, S.D. et al.; Biocidal Polymers; Trends in Polym. Science; Nov. 1996; pp. 364-370; vol. 4, No. 11; Elsevier Science Ltd.
Luo, J. et al.; Acyclic N-Halamine Coated Kevlar Fabric Materials: Preparation and Biocidal Functions; Ind. Eng. Chem. Res.; 2008; pp. 5291-5297; 47; American Chemical Society.
Chen, Z. et al.; Biocidal efficacy, biofilm-controlling function, and controlled release effect of chloromelamine-based bioresponsive fibrous materials; Biomaterials; 2007; pp. 1597-1609; 28; Elsevier Ltd.
Cao, Z. et al.; Polymeric N-Halamine Latex Emulsions for Use in Antimicrobial Paints; ACS Applied Materials & Interfaces; Feb. 4, 2009; pp. 494-504; vol. 1, No. 2.
Sun, Y. et al.; Novel Refreshable N-Halamine Polymeric Biocides: N-Chlorination of Aromatic Polyamides; Ind. Eng. Chem. Res.; 2004; pp. 5015-5020; 43; American Chemical Society.
Ren, X. et al.; N-Halamine-coated cotton for antimicrobial and detoxification applications; Carbohydrate Polymers; 2009; pp. 220-226; 78; Elsevier Ltd.
Dickerson, M. et al.; Sporicidal/Bactericidal Textiles via the Chlorination of Silk; ACS Applied Materials & Interfaces; 2012; pp. 1724-1732; 4; American Chemical Society.
Gottardi, W. et al.; N-chlorotaurine, a natural antiseptic with outstanding tolerability; Journal of Antimicrobial Chemotherapy; Jan. 6, 2010; pp. 399-409; 65.
Qian, L. et al.; Durable and Regenerable Antimicrobial Textiles: Improving Efficacy and Durability of Biocidal Functions; Journal of Applied Polymer Science; 2004; pp. 2588-2593; vol. 91; Wiley Periodicals, Inc.

(Continued)

*Primary Examiner* — Robert A Wax
*Assistant Examiner* — Danah Al-Awadi
(74) *Attorney, Agent, or Firm* — Dinsmore & Shohl LLP

(57) ABSTRACT

A method of forming a biocidal halogenated organic/inorganic composite material may include providing at least one inorganic precursor, providing at least one organic agent, precipitating an organic/inorganic composite material by contacting the at least one inorganic precursor with the at least one organic agent, and halogenating the organic/inorganic composite material by contacting the organic/inorganic composite material with a halogen. Also, a halogenated organic/inorganic composite material may include an inorganic composition comprising a metal oxide and a halogenated organic composition. The inorganic composition and the halogenated organic composition are dispersed throughout the composite material.

38 Claims, 27 Drawing Sheets

(56) References Cited

OTHER PUBLICATIONS

Akdag, A. et al.; The Stabilities of N—Cl Bonds in Biocidal Materials; Journal of Chemical Theory and Computation; Mar. 16, 2006; pp. 879-884; 2; American Chemical Society.

Liang, J. et al.; Improved Antimicrobial Siloxane; Ind. Eng. Chem. Res.; Mar. 6, 2007; pp. 1861-1866; 46; American Chemical Society.

Fei, X. et al.; Pesticide Detoxifying Functions of N-Halamine Fabrics; Archives of Environmental Contamination and Toxicology; 2006; pp. 509-514; 51.

Fei, X. et al.; Kinetics, Catalysis, and Reaction Engineering, Oxidative Degradation of Organophosphorous Pesticides by N-Halamine Fabrics; 2009; pp. 5604-5609; 48; American Chemical Society.

Salter, B. et al.; N-chloramide modified Nomex as a regenerable self-decontaminating material for protection against chemical warfare agents; J. Mater. Sci.; Feb. 26, 2009; pp. 2069-2078; 44; Springer Science+Business Media, LLC.

Liu, S. et al.; New Refreshable N-Halamine Polymeric Biocides: N-Chlorination of Acyclic Amide Grafted Cellulose; Ind. Eng. Chem. Res.; 2009; pp. 613-618; 48; American Chemical Society.

Sun, Y. et al.; Novel Refreshable N-Halamine Polymeric Biocides: Grafting Hydantoin-Containing Monomers onto High Performance Fibers by a Continuous Process; Journal of Applied Polymer Science; 2003; pp. 1032-1039; vol. 88; Wiley Periodicals, Inc.

Luo, J. et al.; Acyclic N-Halamine-Based Fibrous Materials: Preparation, Characterization, and Biocidal Functions; Journal of Polymer Science: Part A: Polymer Chemistry; 2006; pp. 3588-3600; vol. 44; Wiley Periodicals, Inc.

Lin, J. et al.; Biocidal Polyester; Journal of Applied Polymer Science; 2002; pp. 177-182; vol. 85; Wiley Periodicals, Inc.

Chen, Z. et al.; Antimicrobial Polymers Containing Melamine Derivatives. II. Biocidal Polymers Derived from 2-Vinyl-4,6-diamino-1,3,5-triazine; Journal of Polymer Science: Part A: Polymer Chemistry; 2005; pp. 4089-4098; vol. 43; Wiley Periodicals, Inc.

Williams, D. et al.; Is Free Halogen Necessary for Disinfection?; Applied and Environmental Microbiology; Oct. 1988; pp. 2583-2585; vol. 54, No. 10; American Society for Microbiology.

Sun, X. et al.; Electrospun Composite Nanofiber Fabrics Containing Uniformly Dispersed Antimicrobial Agents As an Innovative Type of Polymeric Materials with Superior Antimicrobial Efficacy; ACS Applied Materials & Interfaces; Apr. 9, 2010; pp. 952-956; vol. 2, No. 4.

\* cited by examiner

SEQUENCE LISTING

```
<160> NUMBER OF SEQ ID NOS: 1

<210> SEQ ID NO 1
<211> LENGTH: 33
<212> TYPE: PRT
<213> ORGANISM: Oncorhynchus mykiss

<400> SEQUENCE: 1

Met Pro Arg Arg Arg Arg Ser Ser Ser Arg Pro Val Arg Arg Arg Arg
1               5                   10                  15

Arg Pro Arg Val Ser Arg Arg Arg Arg Arg Gly Gly Arg Arg Arg
            20                  25                  30

Arg
```

SYNTHESIS MODELS FOR ANTIMICROBIAL AGENTS VIA THE HALOGENATION OF ORGANIC/INORGANIC COMPOSITES

PRIORITY

This application claims priority to U.S. Provisional Patent Application No. 61/620,731, filed Apr. 5, 2012, entitled "SYNTHESIS MODELS FOR ANTIMICROBIAL AGENTS VIA THE HALOGENATIONS OF ORGANIC/INORGANIC COMPOSITES."

The subject matter of the present disclosure was made with government support under contract number FA8650-09-D-5037 awarded by the United States Air Force, who have certain rights.

BACKGROUND

1. Field

The present specification generally relates to biocidal materials and methods to form such biocidal materials. More specifically, the present specification relates to a biocidal halogenated composite.

2. Technical Background

Biocidal materials are commonly used to clean or sterilize desired areas from chemical and biological contaminants. Many common household and industrial cleaning agents utilize halogens to oxidize unwanted contaminants such as liquid halogen solutions such as bleach (NaOCl). However, liquid halogen solutions have limitations in some applications. For example, a liquid halogen such as bleach is not desirable for use as a paint additive, surface coating, or filtrate material. Additionally, a convenient source of solid oxidizing halogens would be suitable as a replacement for cleaning agents, such as those containing solid sodium dichloro-s-triazinetrione dihydrate, polishing agents, or combined sanding/oxidizing agents.

There is a need for a solid and convenient source of halogens for many applications. The present specification discloses a solid composite material that can carry halogens and act as a biocidal agent.

SUMMARY

In one embodiment, a method of forming a biocidal halogenated organic/inorganic composite material comprises providing at least one inorganic precursor, providing at least one organic agent, precipitating an organic/inorganic composite material by contacting the at least one inorganic precursor with the at least one organic agent, and halogenating the organic/inorganic composite material by contacting the organic/inorganic composite material with a halogen.

In another embodiment, a halogenated organic/inorganic composite material comprises an inorganic composition comprising a metal oxide and a halogenated organic composition. The inorganic composition and the halogenated organic composition are dispersed throughout the composite material.

These and additional features provided by the embodiments described herein will be more fully understood in view of the following detailed description, in conjunction with the drawings.

DETAILED DESCRIPTION

In one embodiment, a method of forming a biocidal halogenated organic/inorganic composite material comprises providing at least one inorganic precursor, providing at least one organic agent, precipitating an organic/inorganic composite material by contacting the at least one inorganic precursor with the at least one organic agent, and halogenating the organic/inorganic composite material by contacting the organic/inorganic composite material with a halogen.

Figure 1:
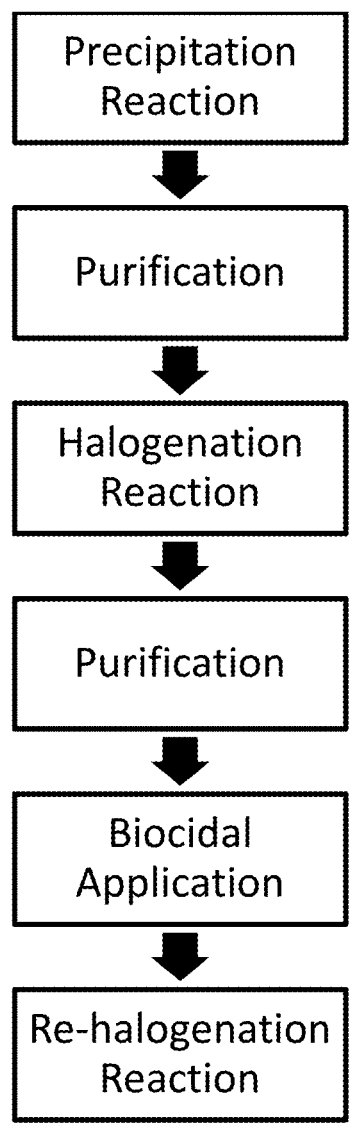
FIG. 1 shows a diagram of the process steps of one embodiment disclosed herein of forming a biocidal halogenated organic/inorganic composite material.

FIG. 1 generally shows a diagram of one embodiment of the process steps of forming a biocidal halogenated organic/inorganic composite material. Generally, a precipitation reaction occurs to form the organic/inorganic composite material. The organic/inorganic composite material may then optionally be purified. The organic/inorganic composite material is then halogenated by contact with a halogen, forming a halogenated organic/inorganic composite material. The halogenated organic/inorganic composite material may then optionally be purified. The halogenated organic/inorganic composite material may then be applied to a chemical or biological material to oxidize the chemical or biological material through contact with the chemical or biological material. The organic/inorganic composite material may then optionally be re-halogenated by contact with a halogen.

Assumed herein, the "inorganic precursor" is a solution which comprises a composition which is capable, when contacted with an organic agent, of precipitating to form an organic/inorganic composite. The inorganic precursor comprises a composition that comprises a metal oxide, metal hydroxide, metal carbonate, metal phosphate, metal oxalate, metal citrate, metal halide, metal sulfate, metal sulfide, metal selenide, and/or metal telluride. The inorganic precipitate formed may be amorphous, semi-crystalline, or crystalline. Metal oxide, as used herein, can mean any oxide of one or more metals or metalloids such as, but not limited to, silica ($SiO_2$) or titania ($TiO_2$), or combinations thereof. In other embodiments, other ceramics, ceramic alloys, and ceramic mixtures may be used as an inorganic precursor. Examples of ceramics that may be used as inorganic precursors include, but are not limited to, $Fe_3O_4$, $Fe_2O_3$, FeO, FeO(OH), FeS, $FeS_2$, $Fe_3S_4$, $SrFe_{12}O_{19}$, $BaFe_{12}O_{19}$, $CoFe_2O_4$, $ZnFe_2O_4$, $BaTiO_3$, $SrTiO_3$, ZnO, $Zn_2SiO_4$, $FeTiO_3$, MgO, $CO_2O_3$, $Al_2O_3$, AlO(OH), $ZrO_2$, $HfO_2$, MnO, $CaCO_3$, $MgCO_3$, CaF, ZnS, CdS, CdSe, CdTe, ZnSe, $CaSO_4$, $SrSO_4$, $MgSO_4$, $Ca_{10}(PO_4)_6(OH)_2$, $Ca_2P_2O_7$ Embodiments of ceramic alloys include, but are not limited to $(Ca_x,Mg_{1-x})CO_3$, $Cd(S_x,Se_{1-x})$, $(Ba_x,Sr_{1-x})TiO_3$, $(Cd_x,Zn_{1-x})S$, $Mg_xCa_{10-x}(PO_4)_6(OH)_2$ In additional embodiments, the doping of metal oxides or other ceramic compositions with rare earth elements including, but not limited to the elements Sc, Y, La, Ce, Pr, Nd, Pm, Sm, Eu, Gd, Tb, Dy, Ho, Er, Tm, Yb, and/or Lu. Examples of rare earth doped ceramics include, but are not limited to, $BaTiO_3:Eu^{3+}$, $ZnO:Eu^{3+}$, and $(La,Ba)TiO_3$. Examples of chemicals that comprise metal oxides, and are suitable inorganic precursors, include silicic acid, $[SiO_x(OH)_{4-2x}]_n$, or titanium(IV) bis(ammonium lactato)dihydroxide (TiBALDH). Examples of chemicals that comprise metal sulfides, and are suitable inorganic precursors, include metal ions produced through the dissolution of a metal salt and sulfide ions from $Na_2S$. Examples of chemicals that comprise metal carbonates, and are suitable inorganic precursors, include metal ions produced through the dissolution of a metal salt such as calcium nitrate and carbonate ions from sodium carbonate, ammonium carbonate, or carbon dioxide gas. Examples of chemicals that comprise metal phosphates, and are suitable inorganic precursors, include metal ions produced through the dissolution of a metal salt such as calcium nitrate, and phosphate ions from phosphoric acid, ammonium phosphate, or sodium phosphate salts. Examples of chemicals that comprise metal sulfates, and are suitable inorganic precursors, include metal ions produced through the dissolution of a metal salt such as calcium chloride, and sulfate ions from sulfuric acid.

Further assumed herein, an "organic agent" is a solution which comprises any organic chemical which is capable, when contacted with an inorganic precursor, of precipitating to form an organic/inorganic composite. The organic agent may comprise one or more biological compositions or at least one synthetic analog of a biological composition. As used herein, a biological composition is any chemical composition relating to life or living matter in all its forms and phenomena.

Further assumed herein, a "halogen" may be any molecule which comprises a halogen atom.

Specifically, an organic agent may comprise any biological composition or synthetic analog of a biological composition that has moieties containing nitrogen. Such nitrogen-containing organic agents may comprise, but are not limited to, organic molecules with amine, amide, imine, and imide functional groups, and combinations thereof.

Various amounts are contemplated herein for the nitrogen containing moieties in the organic agent. In one embodiment, the biological composition or synthetic analog comprises at least 20 wt % organic nitrogen-containing moieties. In another embodiment, the biological composition or synthetic analog comprises at least 30 wt % organic nitrogen-containing moieties. In yet another embodiment, the biological composition or synthetic analog comprises at least 40 wt % organic nitrogen-containing moieties. In yet another embodiment, the biological composition or synthetic analog comprises at least 50 wt % organic nitrogen-containing moieties.

In additional embodiments, the nitrogen-containing biological compositions may include, but are not limited to, peptides, proteins, amino acids, nucleic acids, cells, small organic molecules, and combinations thereof. The nitrogen-containing biological compositions may be used in whole, in portion, in the native state, in a modified state, and/or combinations thereof. These nitrogen containing biological compositions may be obtained from commercial sources, produced in a native or modified organism, such as, but not limited to, inexpensive agricultural or agricultural waste products. In one embodiment, the organic agent comprises a peptide or protein comprising arginine. The organic agent may comprise a peptide or protein wherein at least 25% of the amino acids of the peptide or protein are arginine, or another amino acid which has available nitrogen-containing functional groups available for chlorination. One such peptide suitable for use in an organic agent, is protamine. The biological composition may be synthetically produced. In one embodiment, the biological composition comprises peptides, nucleic acids, or combinations thereof. A synthetically prepared biological composition such as, but not limited to, peptides and nucleic acids may contain "unnatural" functionalities including, but not limited to, amino acid side chains, nucleic bases, or combinations thereof. A biological composition may be chemically modified after it has been biologically or synthetically produced. Native or chemically modified biological compositions may possess inherent antimicrobial activity that can be further augmented by halogenation after the formation of an organic/inorganic composite.

In one embodiment, an organic agent may comprise a nitrogen-containing synthetic analog to a biological composition such as polyamines including, but not limited to, polyethylene imine, polyallyamine, putrescine, spermidine, and combinations thereof. In another embodiment, an organic agent may compromise a nitrogen-containing synthetic analog to a biological composition such as, but not limited to, polyimides including poly(N-vinylguanidine) or oligohexamethyleneguanidine. In another embodiment, an organic agent may compromise a nitrogen-containing synthetic analog to a biological composition such as, but not limited to, peptide nucleic acids, locked nucleic acids, morpholinos, threose nucleic acids, 2'-O-methyl-substituted RNA and in combinations thereof or with other biomolecules. In another embodiment, an organic agent may compromise a nitrogen-containing synthetic analog to a biological composition such as, but not limited to, peptidomimetics including, but not limited to, Bis-peptides, peptoids, oligo urea peptidomimetics, oligopeptidosulfonamides, and combinations thereof or in combinations with other biomolecules. In another embodiment, an organic agent may compromise a nitrogen-containing synthetic analog to a biological composition such as, but not limited to, constrained peptidomimetics, peptides, or hybrids thereof by cyclization, addition of intramolecular hydrocarbon linkages, intramolecular hydrocarbon-azide linkages, and combinations thereof. The nitrogen-containing analogs to biological compositions may be obtained from commercial sources or synthesized.

To precipitate an organic/inorganic composite, the inorganic precursor is contacted with the organic agent to precipitate a solid organic/inorganic composite. Optionally, the precipitation reaction may be accelerated by heating the reaction mixture. In one embodiment, the precipitation reaction is performed at a temperature below 200° C. In another embodiment, the precipitation reaction is performed at a temperature below 100° C. In yet another embodiment, the precipitation reaction is performed at a temperature below 50° C. In yet another embodiment, the precipitation reaction can be performed at a temperature below 30° C., or at room temperature.

An organic/inorganic composite may optionally be purified following precipitation. The organic/inorganic composite may be removed from the reaction solution by centrifugation. The excess reaction solution may be removed by decanting and the particles subsequently rinsed and re-suspended in water. The organic/inorganic composite particles may be further purified through one or more additional centrifugal collection and water rinsing steps.

An organic/inorganic composite may be halogenated (loaded) by contacting the organic/inorganic composite with a halogen. A halogen, as used herein, means any halogen containing compound. The halogen solution comprises halogen molecules comprising halogen atoms such as, but not limited to, chlorine or bromine, and combinations thereof. In one embodiment the halogen bleach (NaOCl).

Without being bound by theory, the halogenation reaction forms covalent bonds between at least some of the nitrogen moieties of the organic composition of the organic/inorganic composite and the halogen atom of the halogen. The halogentated organic-halogen/inorganic composite is now substantially more biocidal than the nonhalogenated organic/inorganic composite. The loading and subsequent release of oxidizing halogens onto/from the nitrogen moieties of the organic composition of the organic/inorganic composite when bleach is used as the chloride may be the reaction shown below:

$$R_1R_2NH + HOCl \leftrightarrow H_2O + R_1R_2NCl$$

where $R_1$ and $R_2$ can and be any chemical constituent contained in the organic precursor.

In one embodiment, additional nitrogen-containing organic agents may be entrapped within the precipitated organic/inorganic composite. These additional, entrapped, nitrogen-containing organic agents may be halogenated in addition to the precipitating organic agent and contribute to the overall activity of the composite. Examples of nitrogen-containing organic agents include, but are not limited to, peptides, proteins, amino acids, nucleic acids, cells, small organic molecules, polymers, synthetic analogs to a biological composition, and combinations thereof. It is contemplated that the additional nitrogen-containing organic agent may be present in the composite material in a concentration or quantity that is less-than, equal to, or greater than the inorganic precipitating organic agent. In one embodiment, an inorganic precipitating organic agent is coated on the surface of a protein-based material or fabric such as, but not limited to, a fibrous material such as, but not limited to, silk, cotton, or wool, where upon contact with an inorganic precursor compound, the protein-based material or fabric is entrapped within a shell of organic/inorganic composite material. Following the formation of the entrapping organic/inorganic composite, the protein-based material or fabric and the organic-constituent of the organic/inorganic composite may be chlorinated.

The organic/inorganic composite described herein may be halogenated multiple times. A composite that has been halogenated can be re-halogenated in a reloading process, where the halogenated organic/inorganic composite is reloaded by further contact with a halogen. At least some of the nitrogen-containing moieties of the halogenated organic/inorganic composite may become unhalogenated gradually over time, or may become unhalogenated from some event, such as a cleaning event, and require the reloading of halogen. The reloading process can take place many times, and in certain embodiments may be required as a maintenance step in maintaining the biocidal trait of the organic/inorganic composite.

In the organic/inorganic composite described herein, the inorganic composition and the organic composition may be dispersed throughout the composite material and may be present in various shapes and forms. As used herein, "dispersed throughout" means that the inorganic composition and the organic composition are distributed throughout or substantially distributed throughout the composite. Without being bound by theory, this distribution or dispersion profile is produced by the composite synthesis methods described herein. In specific embodiments, "dispersed throughout" may also mean homogenously distributed or substantially homogenously distributed. In some embodiments, the precipitated composite particle may be spherically shaped. In one embodiment the composite particles are spherical and are approximately 0.5-5 µm in diameter. In other embodiments, the precipitated composite particle may be shaped as a hexagonal platelet. In another embodiment, the particles possess both hexagonal platelet and spherical morphologies.

Various compositional amounts are contemplated as suitable for the halogenated organic/inorganic composite material. In one embodiment, the halogenated organic/inorganic composite material may comprise about 20 to about 80% by weight of the halogenated organic composition. In another embodiment, the halogenated organic/inorganic composite material may comprise about 20 to about 80% by weight of the inorganic composition. In yet another embodiment, the halogenated organic/inorganic composite material may comprise a ratio by weight of the halogenated organic composition to the inorganic composition of about 1:5 to about 5:1. In yet another embodiment, the halogenated organic/inorganic composite material may comprise a ratio by weight of the halogenated organic composition to the inorganic composition of about 0.8:1 to about 1:0.8. In yet another embodiment, the halogenated organic/inorganic composite material may comprise a ratio by weight of the halogenated organic composition to the inorganic composition of about 1:1 In yet another embodiment, the halogenated organic/inorganic composite material may comprise a ratio by weight of the halogenated organic composition to the inorganic composition of about 0.5:1 to 0.6:1.

The halogenated organic/inorganic composite may be used for decontaminating a toxic chemical or biological agent susceptible to oxidation via halogenation by contacting the chemical or biological agent with the halogenated organic/inorganic composite.

In one embodiment, the organic/inorganic composite can be coated onto a surface, where when chlorinated, these materials may serve to degrade biological and chemical contaminants. The organic/inorganic composite material could be mixed into paint or other surface coating means, and subsequently be painted onto a surface. The organic/inorganic composite on the surface could be loaded (halogenated) through contact with a chloride, such as bleach. The organic/inorganic composite could be periodically reloaded (halogenated) to ensure that the organic/inorganic composite is halogenated and thus biocidal. Similarly, the halogenated organic/inorganic composites may be utilized to deactivate captured biological and chemical contaminants. In one embodiment, the surface may comprise a fibrous material, such as but not limited to, a material comprising plant-based fibers (i.e., cotton, flax), synthetic fibers (i.e., rayon, polyester, aramid, nylon), animal-based fibers (i.e., wool, silk), or combinations thereof. The fibrous material may be in a fabric form.

In another embodiment, the organic/inorganic composite described herein may be used as a source of active halogen for the disinfection/decontamination of water sources. The composite may be especially effective in the disinfection/decontamination of water sources when applied as a coating to filters or when used as a dual purpose halogen-source and filter media.

In another embodiment, when combined with metal powders (e.g., Al) the organic/inorganic composite may be used in ordinance and incendiary devices as the halogen-organic/inorganic composites may uniquely serve as a dual source (organic halamine & inorganic oxide) oxidizer.

In another embodiment, the organic/inorganic composite described herein may be applied to the fabrication of self cleaning surfaces in a variety of settings that may be subject to biological contamination, including but not limited to, bacterial contamination on food preparation surfaces (e.g. cutting boards or knives) or surfaces exposed to continually wet conditions that may produce algal or fungal contamination (e.g., grout/tile in bathrooms or exterior paints). The organic/inorganic materials described herein may be self-decontaminating, and can be used on any desired surface.

In another embodiment, the organic/inorganic composite described herein may be useful for deodorization or odor neutralizations, clean up of decomposition, and neutralizations of biological, chemical, and environmental contaminants.

The organic/inorganic materials described herein may be used as a substitute for halogens, an oxidizing agent, a laundry additive, a cleaning agent, a whitening agent, a disinfectant, or a decontaminant where a halogen such as bleach is used.

EXAMPLES

The following examples are provided by way of illustration and nothing therein should be taken as a limitation upon the overall scope of the claimed subject matter.

Example 1

In this example, the peptide protamine (amino acid sequence: MPRRRRSSSR PVRRRRRPRV SRRRRRRGGR RRR) was utilized both as an agent to induce the precipitation of an inorganic material (silica) and as a nitrogen source for chlorination. Protamine sulfate salt (commercially available from Sigma-Aldrich Co., St. Louis, Mo.) was obtained as a white amorphous powder and combined with 18.2 MΩ (resistivity of 18.2 megaohm-cm) water to produce a stock solution containing 10 mg protamine/ml water. Silicic acid was used as the inorganic precursor, and was prepared by hydrolyzing tetramethoxysilane in 1 mM hydrochloric acid to give a final concentration of 1 M silicic acid. Protamine/silica composite materials were biomimetically synthesized through the preparation of a reaction mixture containing 50 mM, pH 7 sodium phosphate-citrate buffer, 3 mg/ml protamine, and 100 mM silicic acid. The biomimetic silicification reaction was agitated for 10 minutes at 25° C. The protamine contained within this solution catalyzed the condensation of the silicic acid to form spherical silica particles during the course of the reaction. The protamine/silica composite particles were removed from the reaction solution by centrifugation at 5,000 rpm for 5 minutes, the excess reaction solution removed by decanting and the particles subsequently rinsed and re-suspended in 18.2 MΩ water. The protamine/silica particles were further purified through 2 additional centrifugal collection and water rinsing steps.

Following the final rinsing step, protamine/silica composite powders were frozen in liquid nitrogen and dried for 16 hours in a freeze-drying unit. Thermogravimetric analysis conducted to 850° C. in air, indicated that the dried protamine/silica composite contained 64.7 wt % inorganic material and 35.3 wt % pyrolyzable organic constituent.

Figure 2:
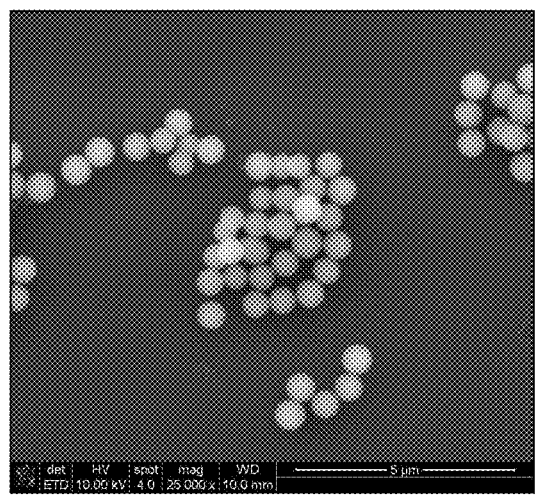
FIG. 2 shows a scanning electron microscope (SEM) image of an unhalogenated protamine/silica composite.

FIG. 2 shows a SEM image of the unhalogenated protamine/silica composite. The unhalogenated protamine/silica composite was determined to be spherical particles of approximately 1 μm in diameter.

Figure 3:
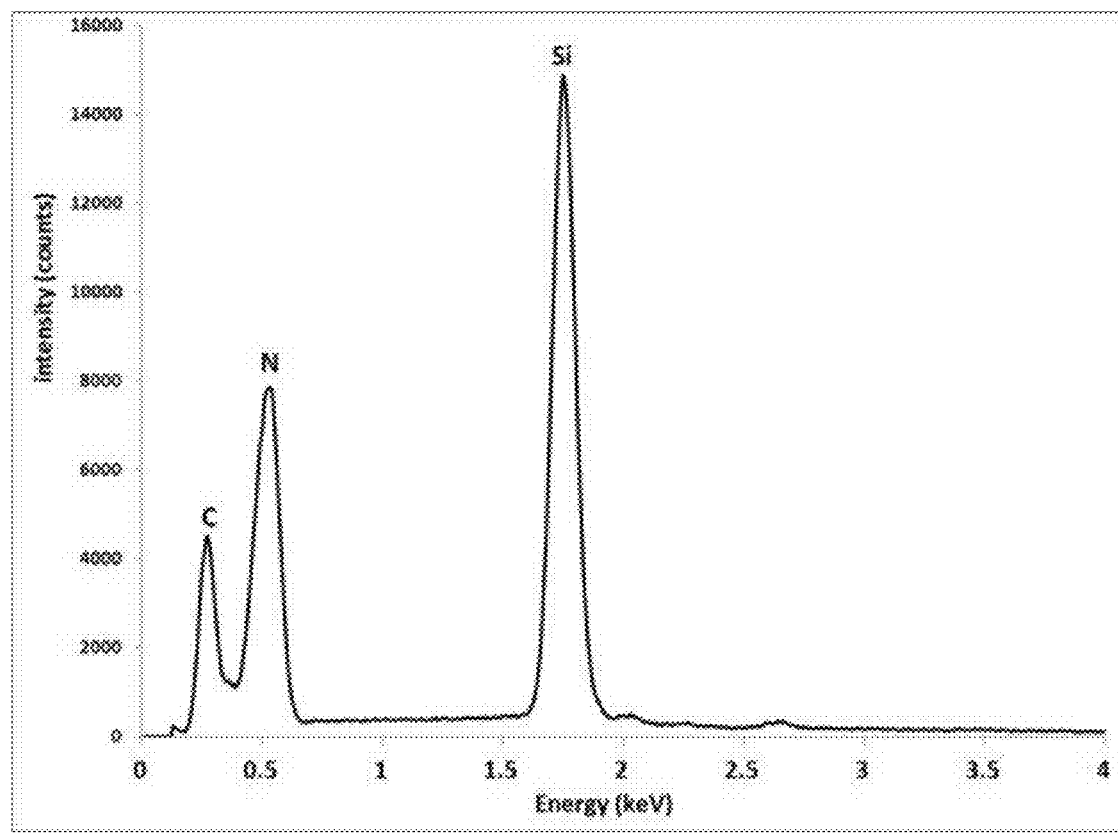
FIG. 3 shows an energy dispersive spectroscopy (EDS) graphical analysis of an unhalogenated protamine/silica composite.

FIG. 3 shows an EDS graphical analysis of the unhalogenated protamine/silica composite. EDS analysis indicated that the as-synthesized protamine/silica composite did not contain appreciable amounts of Cl.

Figure 4:
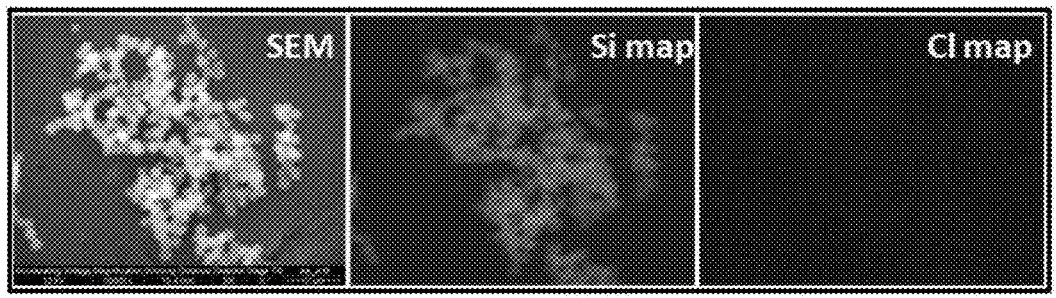
FIG. 4 shows an EDS equipped SEM image of an unhalogenated protamine/silica composite.

FIG. 4 shows an EDS equipped SEM image of the unhalogenated protamine/silica composite. Elemental mapping conducted with an EDS detector-equipped SEM indicated that Si was, but Cl was not, associated with the unhalogenated protamine/silica composite particles.

The protamine contained within the synthesized protamine/silica composite was then chlorinated via a chemical reaction with a chlorine source, NaOCl, through the formation of covalent N—Cl bonds. In this example, the chlorination solution was composed of 10 vol % household bleach (commercially available from Clorox Company, Oakland, Calif.), 0.5 M NaCl, and was pH adjusted to pH 5.0 with 110 mM glacial acetic acid. In this example, 232 mg of protamine/silica composite powder was combined with 45 mL of chlorination solution and agitated for 1 hour. The halogenated protamine-Cl/silica composite particles were removed from the reaction solution by centrifugation at 5,000 rpm for 5 minutes, the excess reaction solution removed by decanting and the chlorinated particles subsequently rinsed and re-suspended in 18.2 MΩ water. The halogenated protamine-Cl/silica composite particles were further purified through 6 additional centrifugal collection and water rinsing steps. The complete removal of the chlorination reaction solution and free Cl from the halogenated protamine-Cl/silica composite materials was verified through the testing of the decanted rinse water with potassium iodide/starch indicator papers (commercially available from Thermo Fisher Scientific Inc., Pittsburgh, Pa.), that detect low levels of chlorine. Following the final rinsing step, halogenated protamine-Cl/silica composite powders were frozen in liquid nitrogen and dried for 16 hours in a freeze-drying unit. Thermogravimetric analysis conducted to 850° C. in air, indicated that the dried halogenated protamine-Cl/silica composite materials contained 65.5 wt % inorganic material and 34.5 wt % pyrolyzable organic constituent. The active chlorine content of the halogenated protamine/silica composite was determined by iodometric titration, utilizing a starch indicator end point to be 6.5 mmol Cl/g material.

Figure 5:
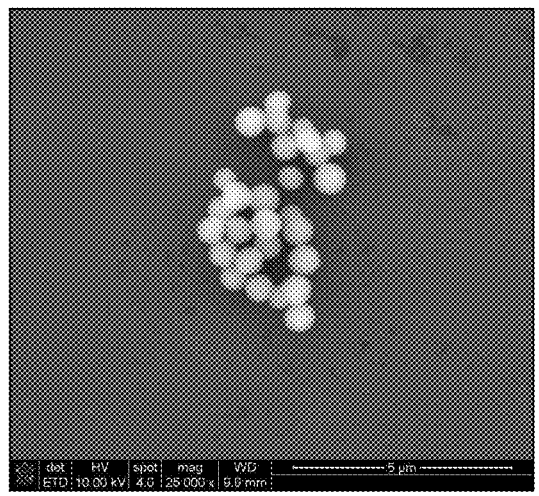
FIG. 5 shows a SEM image of a halogenated protamine/silica composite.

FIG. 5 shows a SEM image of a halogenated protamine-Cl/silica composite. SEM imaging revealed that the morphology of the halogenated protamine-Cl/silica composite was unaffected by the chlorination process.

Figure 6:
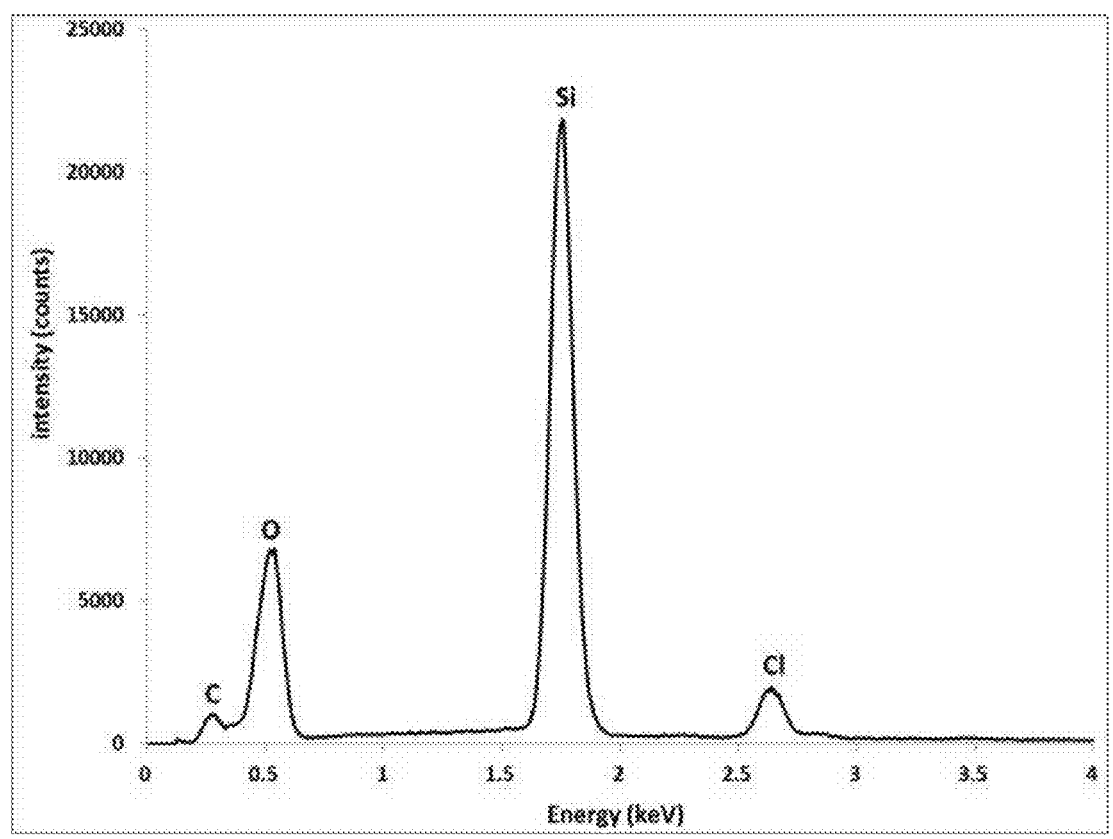
FIG. 6 shows an EDS graphical analysis of a halogenated protamine/silica composite.

FIG. 6 shows an EDS analysis of a halogenated protamine-Cl/silica composite. EDS analysis indicated that the halogenated protamine-Cl/silica composite contained appreciable amounts of Cl.

Figure 7:
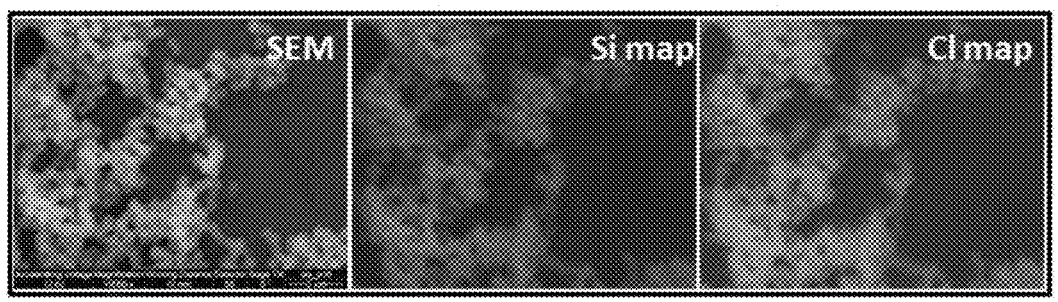
FIG. 7 shows an EDS equipped SEM image of a halogenated protamine/silica composite.

FIG. 7 shows an EDS equipped SEM image of a halogenated protamine-Cl/silica composite. Elemental mapping indicated that Cl was closely associated with Si and was consistent with the SEM observable morphology of the materials.

The antimicrobial activity of the prepared unhalogenated protamine/silica and halogenated protamine-Cl/silica composites were assessed in trials against vegetative *Escherichia coli* strain K12 (gram negative), *Staphylococcus aureus* (gram positive), and *Bacillus thuringiensis* strain Al Hakam (gram positive) cells, as well as dormant *B. thuringiensis* Al Hakam endospores. In this example, cultures of *E. coli* K12 and *S. aureus* were grown for 16 hours at 37° C. with shaking at 200 rpm in LB broth, Miller (commercially available from Amresco LLC., Solon, Ohio) and *B. thuringiensis* Al Hakam cells were grown at 37° C. for 24 hours with shaking at 220 rpm in Nutrient Broth (commercially available from BD Diagnostics). Subsequent to culturing, the bacterial cells were collected by centrifugation at 5,000-10,000 rpm for 5 minutes, the growth broth was decanted and the cells rinsed and resuspended in an equivalent volume of sterile pH 7.4 sodium/potassium phosphate-buffered saline (PBS). The bacterial cells were collected by centrifugation and rinsed with sterile PBS 3 times. Following rinsing the vegetative cells were suspended in a desired volume of PBS. *B. thuringiensis* Al Hakam spore suspensions were prepared by incubating a vegetative culture for 3 days in 50 mL Nutrient Broth, CCY salts, and glutamate at 34° C. with rotation at 220 rpm then washing 8 times by centrifuging at 6,000 rpm for 5 min and re-suspending the pellet in 4 mL 0.1% Tween-80. Upon the final wash, the pellet was re-suspended in 2 mL 0.1% Tween-80, divided into 4 aliquots, and frozen at −80° C. On the day of experimentation, the *B. thuringiensis* spores were diluted to $10^8$ CFU/mL in Gibco® sterile PBS.

In this example, 0.1 g samples (at least 3 samples for each organism tested against) of halogenated protamine-Cl/silica composite were exposed to 1 mL of sterile PBS containing vegetative bacterial cells or dormant *B. thuringiensis* Al Hakam endospores for 10 minutes with gentle agitation (in order to keep particles and bacteria suspended). *E. coli* and *S. aureus* cells were tested at concentrations of $10^{11}$ cfu/ml and *B. thuringiensis* cells and endospores were utilized at a concentration of $10^8$ cfu/ml. After 10 minutes, the antimicrobial action of the halogenated protamine-Cl/silica composites was neutralized through the addition of 0.75 mL of sterile PBS containing 3 wt % $Na_2S_2O_3$ (a recognized chlorine neutralizing agent). An aliquot of the bacterial/silica suspension was removed and utilized to prepare serially diluted samples for plating. Experiments utilizing unhalogenated protamine/silica composite and positive control samples (bacteria only, no protamine/silica composite) (at least 3 experiments for all samples) were conducted in parallel and utilized the same procedure as described for halogenated protamine-Cl/silica composite. Serially diluted samples were plated according to the drop plate method onto LB agar or spread onto nutrient broth agar plates. Plates were inverted and incubated for 16 hours at 37° C. and colonies were counted to determine the bactericidal or sporicidal activity of the materials. The antimicrobial activity of the tested materials is presented in Table 1. As detailed in Table 1, at least about 6.5 Log reduction in the colony forming units of the bacterial cells or spores was obtained when the organisms were brought into contact with halogenated protamine-Cl/silica composite for 10 minutes. In contrast, unhalogenated protamine/silica composite powders induced less than a 2 Log reduction in the colony forming units of the bacterial cells or spores.

TABLE 1

| | Log reduction in CFU (compared to positive control) | | | |
|---|---|---|---|---|
| Material tested | *B. thuringiensis* spores | *B. thuringiensis* cells | *S. aureus* cells | *E. coli* cells |
| halogenated protamine-Cl/ silica composite | 6.5 | >7 | >10 | >10 |
| unhalogenated protamine/ silica composite | 1.4 | 0.292 | 1.65 | 0.83 |

Example 2

In this example, it is demonstrated that the inorganic precipitating agent, and not the inorganic constituent of the composite, is halogenated by chemical reactions with a halogen. As described in detail below, this was accomplished by utilizing protamine to induce the precipitation of silica, forming protamine/silica composite materials. Following synthesis, protamine was removed from the protamine/silica composites by pyrolysis and the resulting materials subjected to a chlorination reaction.

In this example, the peptide protamine (amino acid sequence: MPRRRRSSSR PVRRRRRPRV SRRRRRRGGR RRR) was utilized as an agent to induce the precipitation of an inorganic material (silica). Protamine sulfate salt (commercially available from Sigma-Aldrich Co., St. Louis, Mo.) as a white amorphous powder was combined with 18.2 MΩ (resistivity of 18.2 megaohm-cm) water to produce a stock solution containing 10 mg protamine/ml water. Silicic acid was used as the inorganic precursor, and was prepared by hydrolyzing tetramethoxysilane in 1 mM hydrochloric acid to give a final concentration of 1 M silicic acid. Protamine/silica composite materials were biomimetically synthesized through the preparation of a reaction mixture containing 50 mM, pH 7 sodium phosphate-citrate buffer, 3 mg/ml protamine, and 100 mM silicic acid. The biomimetic silicification reaction was agitated for 10 minutes at 25° C. The protamine contained within this solution condensed the silicic acid to form spherical silica particles during the course of the reaction. The protamine/silica particles were removed from the reaction solution by centrifugation at 5,000 rpm for 5 minutes, the excess reaction solution removed by decanting and the particles subsequently rinsed and re-suspended in 18.2 MΩ water. The protamine/silica composite particles were further purified through 2 additional centrifugal collection and water rinsing steps. Following the final rinsing step, protamine/silica composite powders were frozen in liquid nitrogen and dried for 16 hours in a freeze-drying unit. In order to remove protamine from the protamine/silica composites (0.303 g) the dried powders were placed into a fused-quartz crucible and heated at 400° C. for 4 hours in air. Following this pyrolysis treatment, 0.196 g of material was recovered (64.7% of the initial powder weight), corresponding well with the expected loss of about 35 wt % of pyrolyzable organic constituent (i.e., protamine).

The resulting pyrolyzed protamine/silica composite material was subjected to the chlorination conditions described in Example 1. In this example, the chlorination solution was composed of 10 vol % household bleach (commercially available from Clorox Company, Oakland, Calif.), 0.5 M NaCl, and was pH adjusted to pH 5.0 with 110 mM glacial acetic acid. In this example, about 59 mg samples (at least 3 samples) of pyrolyzed protamine/silica composite was combined with 15 mL of chlorination solution and agitated for 1 hour. The pyrolyzed protamine/silica composite particles were removed from the reaction solution by centrifugation at 5,000 rpm for 5 minutes, the excess reaction solution removed by decanting and the particles subsequently rinsed and re-suspended in 18.2 MΩ water. The pyrolyzed protamine/silica composite particles were further purified through 6 additional centrifugal collection and water rinsing steps. The complete removal of the chlorination reaction solution and free Cl from the pyrolyzed protamine/silica composite materials was verified through the testing of the decanted rinse water with potassium iodide/starch indicator papers (commercially available from Thermo Fisher Scientific Inc., Pittsburgh, Pa.) that detect low levels of chlorine. Following the final rinsing step, pyrolyzed protamine/silica composite powders were frozen in liquid nitrogen and dried for 16 hours in a freeze-drying unit.

The pyrolyzed protamine/silica powders subjected to the chlorination reaction were not found to contain chlorine by iodometric titration, utilizing a starch indicator end point.

Figure 8:
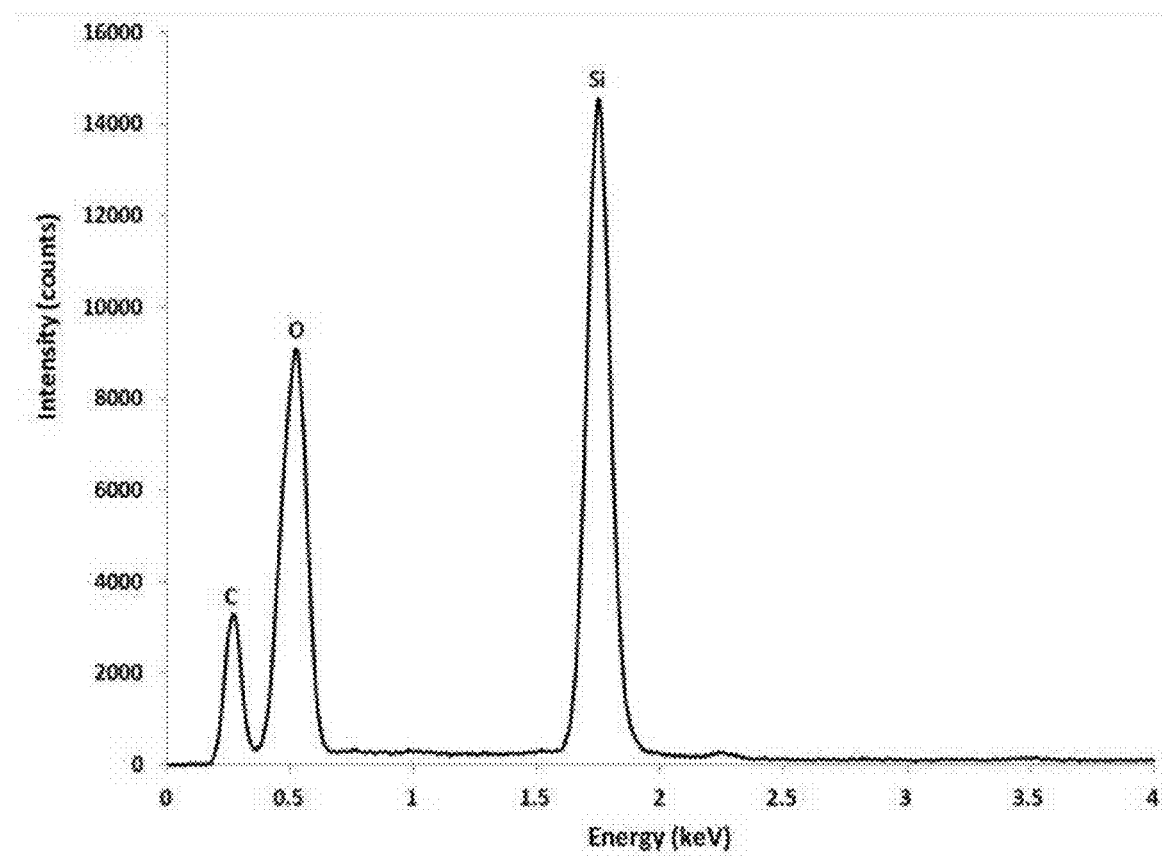
FIG. 8 shows an EDS analysis of a pyrolyzed protamine/silica composite that was halogenated.

FIG. 8 shows an EDS analysis of a pyrolyzed protamine/silica composite that was halogenated. EDS analysis indicated that the pyrolyzed protamine/silica composite material subjected to the chlorination reaction did not contain detectable appreciable amounts of Cl (FIG. 2a).

Figure 9:
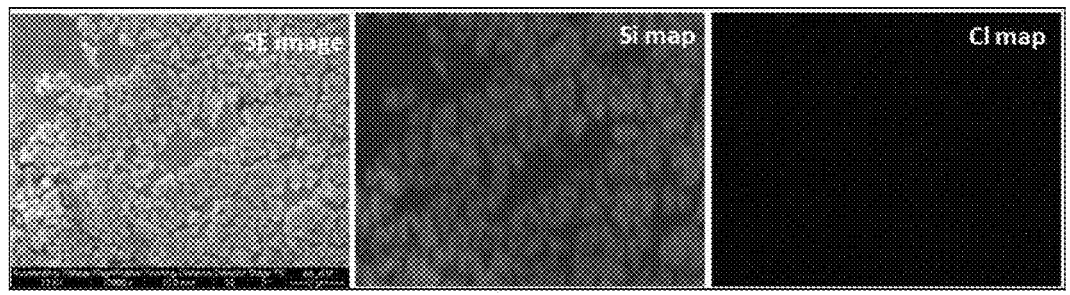
FIG. 9 shows an EDS equipped SEM image of a pyrolyzed protamine/silica composite that was halogenated.

FIG. 9 shows an EDS equipped SEM image of a pyrolyzed protamine/silica composite that was halogenated. Elemental mapping indicated that Cl was absent from, and Si present in, the pyrolyzed protamine/silica composite.

Example 3

In this example, the synthetic peptide mimic, polyethylene imine was utilized both as an agent to induce the precipitation of an inorganic material and as a nitrogen source for chlorination. Polyethylene imine (PEI) is a branched polymer containing primary, secondary, and tertiary amines. The PEI used in this example was a 50 wt % solution in water, having an average molecular weight of about 750,000 (commercially available from Sigma-Aldrich Co. St. Louis, Mo.). The PEI solution was combined with 18.2 MΩ (resistivity of 18.2 megaohm-cm) water to produce a stock solution containing 10 wt % PEI in water. Silicic acid was used as the inorganic precursor, and was prepared by hydrolyzing tetramethoxysilane in 1 mM hydrochloric acid to give a final concentration of 1 M silicic acid. PEI/silica composite materials were biomimetically synthesized through the preparation of a reaction mixture containing 50 mM, pH 7 sodium phosphate-citrate buffer, 1 wt % PEI, and 100 mM silicic acid. The biomimetic silicification reaction was agitated for 10 minutes at 25° C. The PEI contained within this solution condensed the silicic acid to form spherical silica particles during the course of the reaction. The PEI/silica composite particles were removed from the reaction solution by centrifugation at 5,000 rpm for 5 minutes, the excess reaction solution removed by decanting and the particles subsequently rinsed and re-suspended in 18.2 MΩ water. The PEI/silica composite particles were further purified through 2 additional centrifugal collection and water rinsing steps. Following the final rinsing step, PEI/silica composite powders were frozen in liquid nitrogen and dried for 16 hours in a freeze-drying unit.

Figure 10:
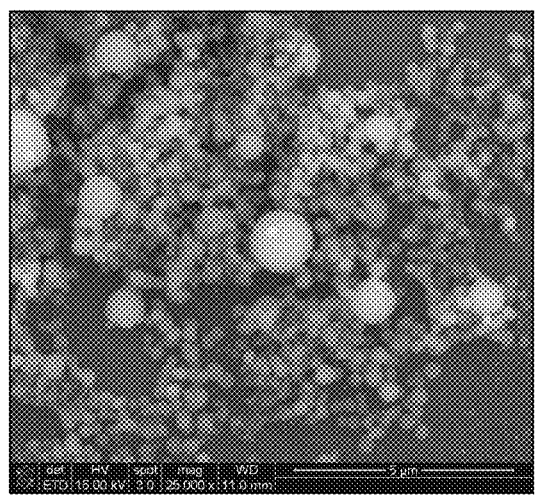
FIG. 10 shows a SEM image of an unhalogenated polyethylene imine/silica composite.

FIG. 10 shows a SEM image of the unhalogenated PEI/silica composite. The unhalogenated PEI/silica composite was determined to be spherical particles approximately 0.5-5 μm in diameter.

Figure 11:
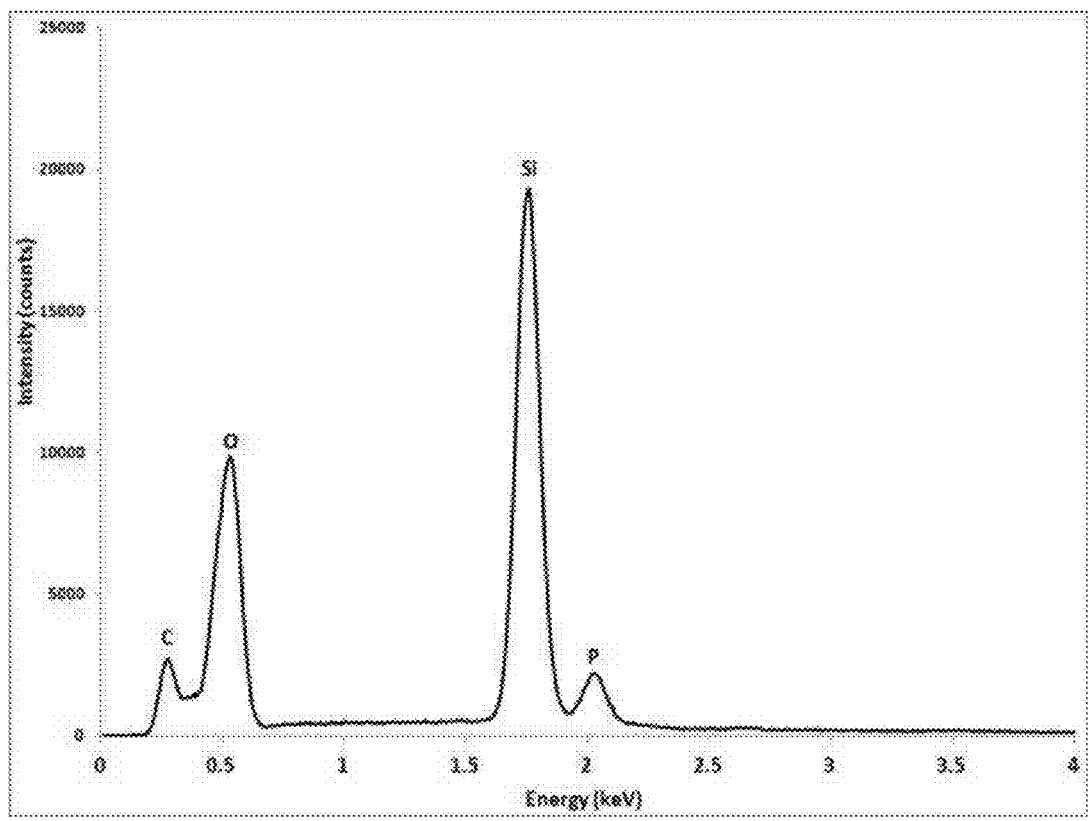
FIG. 11 shows a graphical analysis of an unhalogenated polyethylene imine/silica composite.

FIG. 11 shows an EDS graphical analysis of the unhalogenated PEI/silica composite. EDS analysis indicated that the as-synthesized PEI/silica composite material did not contain appreciable amounts of Cl.

Figure 12:
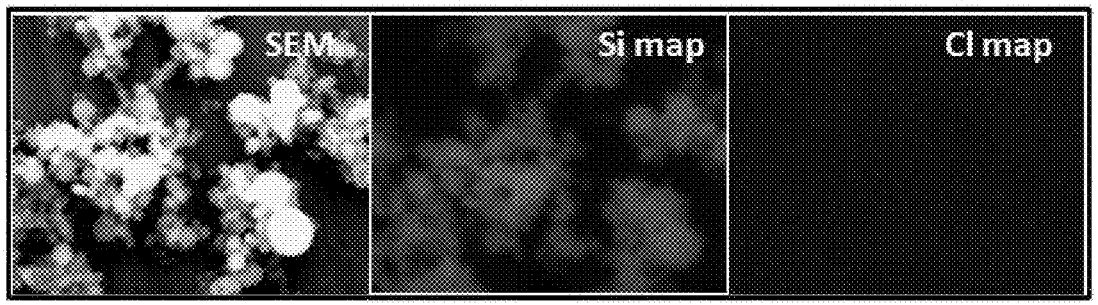
FIG. 12 shows an EDS equipped SEM image of an unhalogenated polyethylene imine/silica composite.

FIG. 12 shows an EDS equipped SEM image of an unhalogenated PEI/silica composite. Elemental mapping conducted with an EDS detector-equipped SEM indicated that Si was, but Cl was not, associated with the PEI/silica composite particles.

The available amines carried by the PEI constituent of the synthesized PEI/silica composite material were chlorinated via a chemical reaction with a chlorine source (NaOCl), through the formation of covalent N—Cl bonds. In this example, the chlorination solution was composed of 10 vol % household bleach (commercially available from Clorox Company, Oakland, Calif.), 0.5 M NaCl, and was pH adjusted to pH 5.0 with 110 mM glacial acetic acid. In this example, 243 mg of PEI/silica composite powder was combined with 45 mL of chlorination solution and agitated for 1 hour. The halogenated PEI-Cl/silica composite particles were removed from the reaction solution by centrifugation at 5,000 rpm for 5 minutes, the excess reaction solution removed by decanting and the chlorinated particles subsequently rinsed and re-suspended in 18.2 MΩ water. The halogenated PEI-Cl/silica particles were further purified through 9 additional centrifugal collection and water rinsing steps. The complete removal of the chlorination reaction solution and free Cl from the halogenated PEI-Cl/silica composite was verified through the testing of the decanted rinse water with potassium iodide/starch indicator papers (commercially available from Thermo Fisher Scientific Inc., Pittsburgh, Pa.) that detect low levels of chlorine. Following the final rinsing step, halogenated PEI-Cl/silica composite powders were frozen in liquid nitrogen and dried for 16 hours in a freeze-drying unit. The active chlorine content of the halogenated PEI-Cl/silica composite was determined by iodometric titration, utilizing a starch indicator end point of 5.1 mmol Cl/g material.

Figure 13:
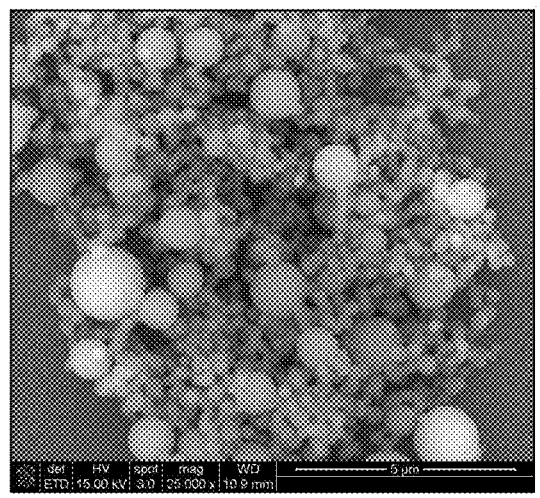
FIG. 13 shows a SEM image of a halogenated polyethylene imine/silica composite.

FIG. 13 shows a SEM image of a halogenated PEI-Cl/silica composite. SEM imaging revealed that the morphology of the PEI-Cl/silica materials was unaffected by the chlorination process.

Figure 14:
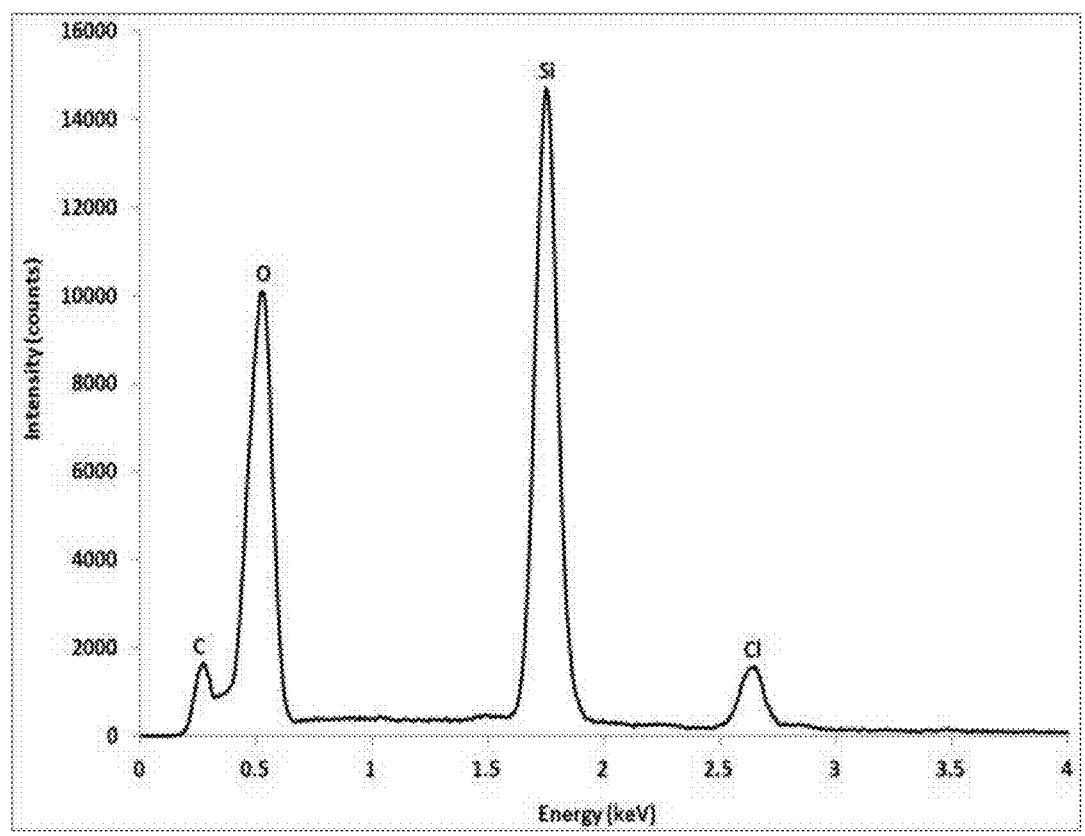
FIG. 14 shows an EDS graphical analysis of a halogenated polyethylene imine/silica composite.

FIG. 14 shows an EDS analysis of a halogenated protamine-Cl/silica composite. EDS analysis indicated that the halogenated protamine-Cl/silica composite contained appreciable amounts of Cl.

Figure 15:
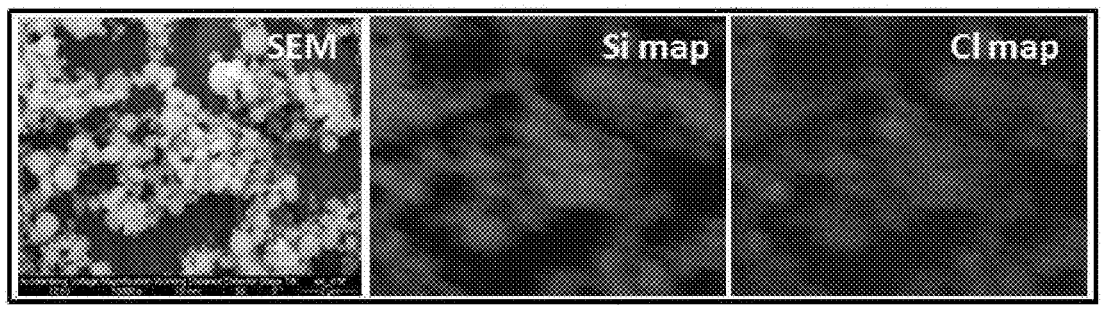
FIG. 15 shows an EDS equipped SEM image of a halogenated polyethylene imine-Cl/silica composite.

FIG. 15 shows an EDS equipped SEM image of a halogenated PEI-Cl/silica composite. Elemental mapping indicated that Cl was closely associated with Si and was consistent with the SEM observable morphology of the materials.

The antimicrobial activity of the prepared unhalogenated PEI/silica and halogenated PEI-Cl/silica composite materials was assessed in trials against vegetative *Escherichia coli* strain K12 (gram negative) and *Staphylococcus aureus* cells. In this example, cultures of *E. coli* K12 and *S. aureus* were grown for 16 hours at 37° C. with shaking at 200 rpm in LB broth, Miller (commercially available from Amresco LLC., Solon, Ohio). Subsequent to culturing, the bacterial cells were collected by centrifugation at 5,000 rpm for 5 minutes, the growth broth was decanted and the cells rinsed and resuspended in an equivalent volume of sterile pH 7.4 sodium/potassium phosphate-buffered saline (PBS). The bacterial cells were collected by centrifugation and rinsed with sterile PBS for a total of 3 times. Following rinsing the vegetative cells were suspended in a desired volume of PBS.

In this example, 0.1 g samples (at least 3 samples for each organism tested against) of halogenated PEI-Cl/silica composite were exposed to 1 mL of sterile PBS containing vegetative bacterial cells for 10 minutes with gentle agitation (in order to keep particles and bacteria suspended). E. coli and S. aureus cells were tested at concentrations of $10^{11}$ cfu/ml.

After 10 minutes, the antimicrobial action of the powders was neutralized through the addition of 0.75 mL of sterile PBS containing 3 wt % $Na_2S_2O_3$ (a recognized chlorine neutralizing agent). An aliquot of the bacterial/silica suspension was removed and utilized to prepare serially diluted samples for plating. Experiments utilizing unhalogenated PEI/silica composite and positive control samples (bacteria only, no PEI/silica composite) (at least 3 experiments for all samples) were conducted in parallel and utilized the same procedure as described for PEI-Cl/silica composite materials. Serially diluted samples were plated according to the drop plate method onto LB agar plates. Plates were inverted and incubated for 16 hours at 37° C. and colonies were counted to determine the bactericidal activity of the materials. The antimicrobial activity of the tested materials is presented in Table 2. As detailed in Table 2, 100% of the bacterial cells (0 colonies counted on plates at any dilution) were killed when brought into contact with halogenated PEI-Cl/silica composite for 10 minutes. In contrast, unhalogenated PEI/silica induced less than a 2 Log reduction in the colony forming units of the bacterial cells.

TABLE 2

| Material tested | Log reduction in CFU (compared to positive control) | |
|---|---|---|
| | S. aureus cells | E. coli cells |
| halogenated PEI-Cl/silica composite | >10 | >10 |
| unhalogenated PEI/silica composite | 0.27 | 1.2 |

Example 4

In this example, the peptide protamine (amino acid sequence: MPRRRRSSSR PVRRRRRPRV SRRRRRRGGR RRR) was utilized both as an agent to induce the precipitation of an inorganic material (titania) and as a nitrogen source for chlorination. Protamine sulfate salt (commercially available from Sigma-Aldrich Co., St. Louis, Mo.) as a white amorphous powder was combined with 18.2 MΩ (resistivity of 18.2 megaohm-cm) water to produce a stock solution containing 10 mg protamine/ml water. Titanium bis(ammoniumlactato)dihydroxide (TiBALDH) solution, 50 wt % in water, was used as the inorganic precursor (commercially available from Sigma-Aldrich Co., St. Louis, Mo.). Protamine/titania composite materials were biomimetically synthesized through the preparation of a reaction mixture containing 50 mM, pH 7 sodium phosphate-citrate buffer, 2 mg/ml protamine, and 100 mM TiBALDH. The biomimetic titania formation reaction was agitated for 10 minutes at 25° C. The protamine contained within this solution interacted with the TiBALDH precursor to form protamine/titania composite particles during the course of the reaction. The protamine/titania composite particles were removed from the reaction solution by centrifugation at 10,000 rpm for 5 minutes, the excess reaction solution removed by decanting and the particles subsequently rinsed and re-suspended in 18.2 MΩ water. The protamine/titania composite particles were further purified through 2 additional centrifugal collection and water rinsing steps.

Following the final rinsing step, protamine/titania composite powders were frozen in liquid nitrogen and dried for 16 hours in a freeze-drying unit. Thermogravimetric analysis conducted to 850° C. in air, indicated that the dried protamine/titania composite contained 60.3 wt % inorganic material and 39.7 wt % pyrolyzable organic constituent.

Figure 16:
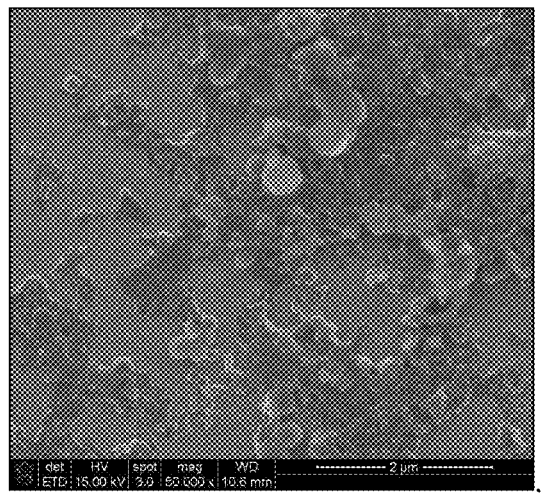
FIG. 16 shows a SEM image of an unhalogenated protamine/titania composite.

FIG. 16 shows a SEM image of an unhalogenated protamine/titania composite. The unhalogenated protamine/titania composite was determined to be particles approximately less than 1 μm in diameter.

Figure 17:
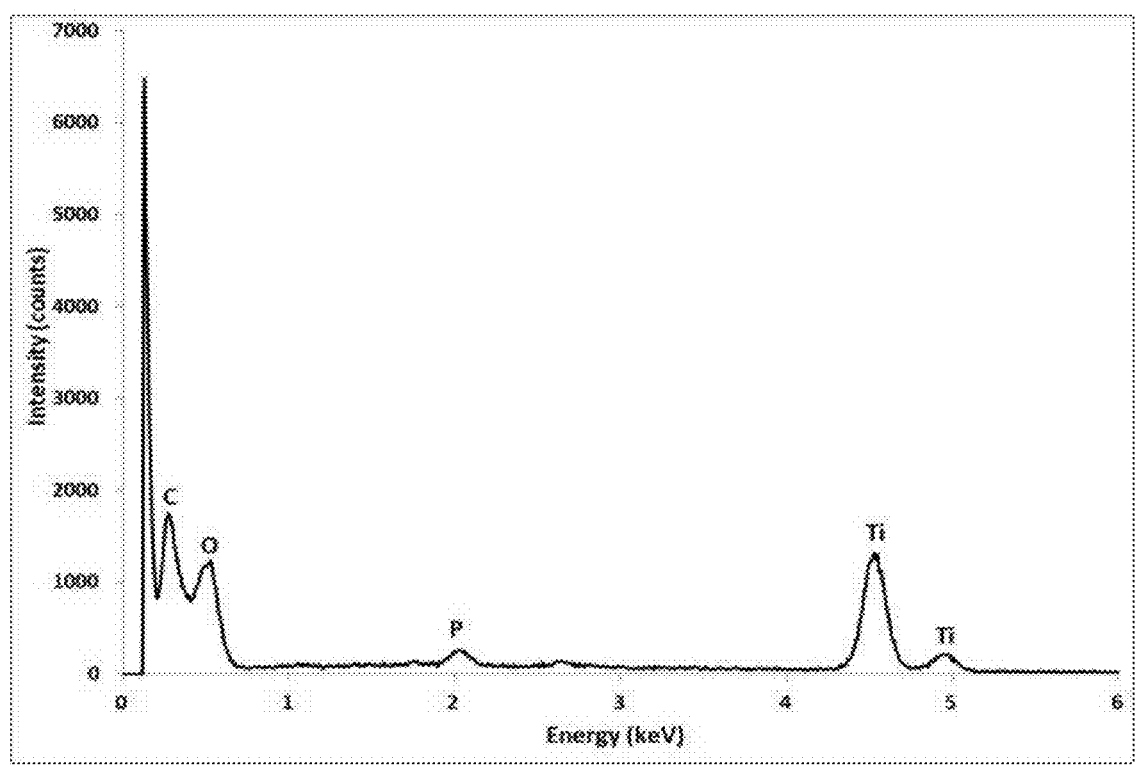
FIG. 17 shows an EDS graphical analysis of an unhalogenated protamine/titania composite.

FIG. 17 shows an EDS analysis of an unhalogenated protamine/titania composite. EDS analysis indicated that the as-synthesized protamine/titania composite material did not contain detectable amounts of Cl.

Figure 18:
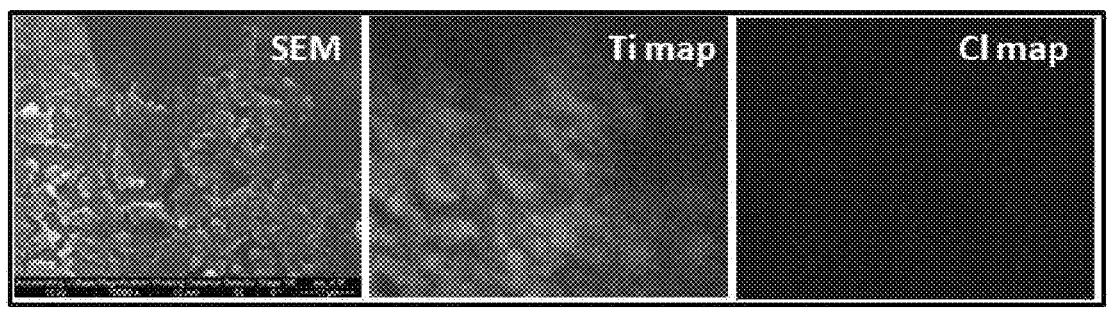
FIG. 18 shows an EDS equipped SEM image of an unhalogenated protamine/titania composite.

FIG. 18 shows an EDS equipped SEM image of an unhalogenated protamine/titania composite. Elemental mapping indicated that Ti was, but Cl was not, associated with the unhalogenated protamine/titania composite particles.

The protamine contained within the synthesized protamine/titania composite was then chlorinated via a chemical reaction with a chlorine source (NaOCl), through the formation of covalent N—Cl bonds. In this example, the chlorination solution was composed of 10 vol % household bleach (commercially available from Clorox Company, Oakland, Calif.), 0.5 M NaCl, and was pH adjusted to pH 5.0 with 110 mM glacial acetic acid. In this example, 170.4 mg of protamine/titania composite powder was combined with 45 mL of chlorination solution and agitated for 1 hour. The halogenated protamine-Cl/titania composite particles were removed from the reaction solution by centrifugation at 10,000 rpm for 5 minutes, the excess reaction solution removed by decanting and the chlorinated particles subsequently rinsed and re-suspended in 18.2 MΩ water. The halogenated protamine-Cl/titania composite particles were further purified through at least about 6 additional centrifugal collection and water rinsing steps. The complete removal of the chlorination reaction solution and free Cl from the halogenated protamine-Cl/titania composite was verified through the testing of the decanted rinse water with potassium iodide/starch indicator papers (commercially available from Thermo Fisher Scientific Inc., Pittsburgh, Pa.) that detect low levels of chlorine. Following the final rinsing step, halogenated protamine-Cl/titania powders were frozen in liquid nitrogen and dried for 16 hours in a freeze-drying unit. Thermogravimetric analysis conducted to 850° C. in air, indicated that the dried halogenated protamine-Cl/titania composite contained 60.9 wt % inorganic material and 39.1 wt % pyrolyzable organic constituent. The active chlorine content of the halogenated protamine-Cl/titania composite was determined by iodometric titration, utilizing a starch indicator end point to be 3.7 mmol Cl/g material.

Figure 19:
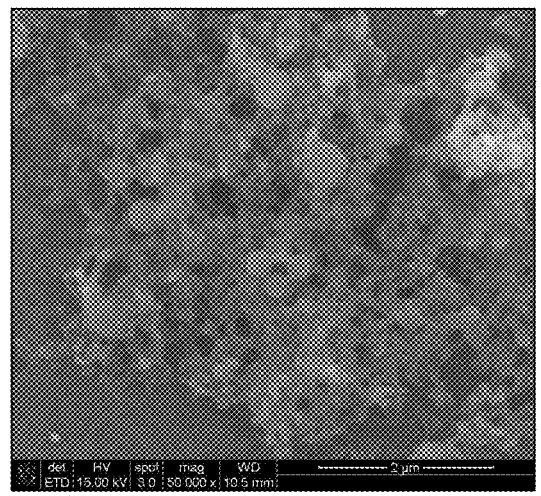
FIG. 19 shows a SEM image of a halogenated protamine/titania composite.

FIG. 19 shows an EDS equipped SEM image of a halogenated protamine-Cl/titania composite. SEM imaging revealed that the morphology of the protamine-Cl/titania composite materials was unaffected by the chlorination process.

Figure 20:
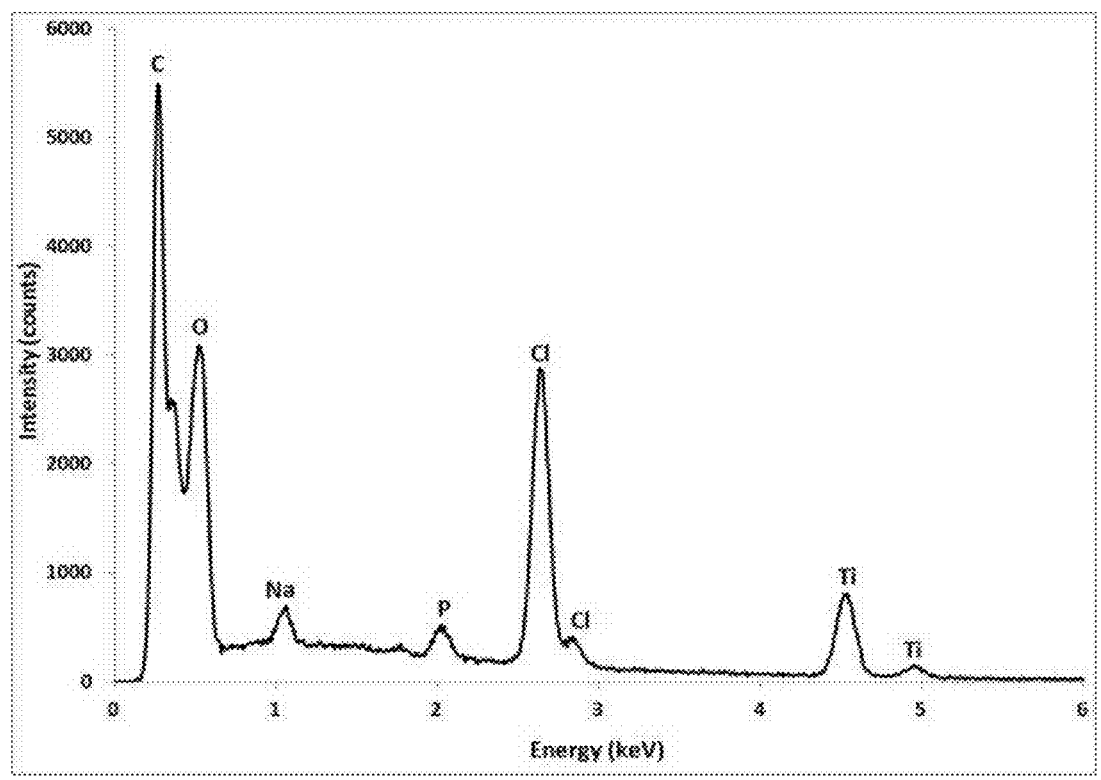
FIG. 20 shows an EDS graphical analysis of a halogenated protamine/titania composite.

FIG. 20 shows a SEM image of a halogenated protamine-Cl/titania composite. EDS analysis indicated that the halogenated protamine-Cl/titania composite contained appreciable amounts of Cl.

Figure 21:
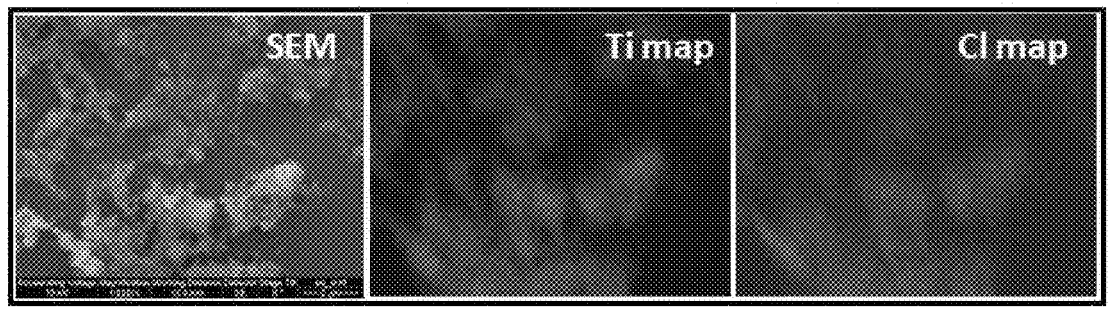
FIG. 21 shows an EDS equipped SEM image of a halogenated protamine-Cl/titania composite.
Figure 22:
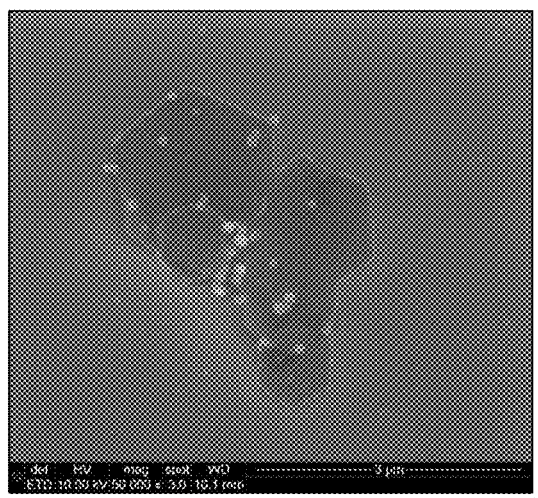
FIG. 22 shows a SEM image of an unhalogenated poly-L-lysine/silica composite.
Figure 23:
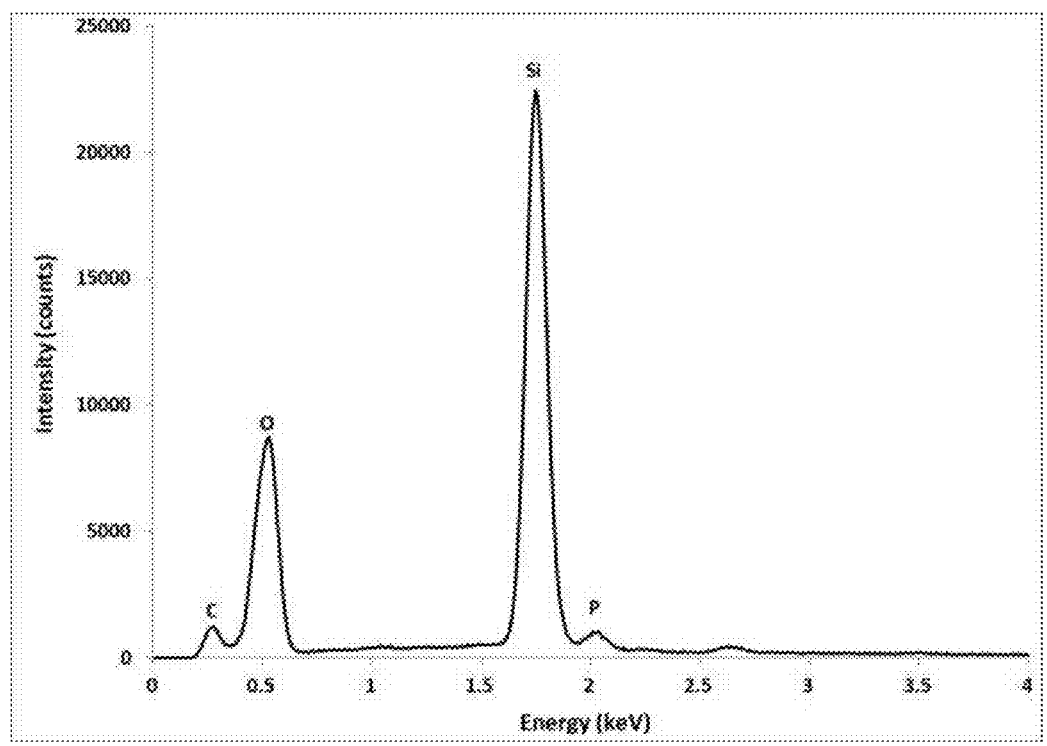
FIG. 23 shows an EDS graphical analysis of an unhalogenated poly-L-lysine/silica composite.
Figure 24:
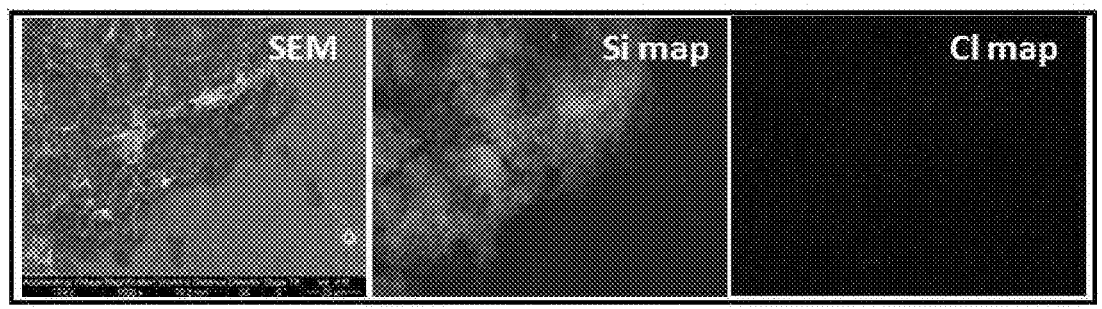
FIG. 24 shows an EDS equipped SEM image of an unhalogenated poly-L-lysine/silica composite.

FIG. 21 shows an EDS analysis of a halogenated protamine-Cl/titania composite. Elemental mapping indicated that Cl was closely associated with Ti and was consistent with the SEM observable morphology of the materials.

The antimicrobial activity of the prepared unhalogenated protamine/titania and halogenated protamine-Cl/titania composites were assessed in trials against vegetative *Escherichia coli* strain K12 (gram negative), *Staphylococcus aureus* (gram positive), and *Bacillus thuringiensis* strain Al Hakam (gram positive) cells, as well as dormant *B. thuringiensis* Al Hakam endospores. In this example, cultures of *E. coli* K12 and *S. aureus* were grown for 16 hours at 37° C. with shaking at 200 rpm in LB broth, Miller (commercially available from Amresco LLC., Solon, Ohio), and *B. thuringiensis* Al Hakam cells were grown at 37° C. for 24 hours with shaking at 220 rpm in Nutrient Broth (commercially available from BD Diagnostics). Subsequent to culturing, the bacterial cells were collected by centrifugation at 5,000-10,000 rpm for 5 minutes, the growth broth was decanted and the cells rinsed and resuspended in an equivalent volume of sterile pH 7.4 sodium/potassium phosphate-buffered saline (PBS). The bacterial cells were collected by centrifugation and rinsed with sterile PBS 3 times. Following rinsing the vegetative cells were suspended in a desired volume of pH PBS. *B. thuringiensis* Al Hakam spore suspensions were prepared by incubating a vegetative culture for 3 days in 50 mL Nutrient Broth, CCY salts, and glutamate at 34° C. with rotation at 220 rpm then washing 8 times by centrifuging at 6,000 rpm for 5 min and re-suspending the pellet in 4 mL 0.1% Tween-80. Upon the final wash, the pellet was re-suspended in 2 mL 0.1% Tween-80, divided into 4 aliquots, and frozen at −80° C. On the day of experimentation, the *B. thuringiensis* spores were diluted to $10^8$ CFU/mL in Gibco® sterile PBS.

In this example, 0.1 g samples (at least 3 samples for each organism tested against) of halogenated protamine-Cl/titania composite were exposed to 1 mL of sterile PBS containing vegetative bacterial cells or dormant *B. thuringiensis* Al Hakam endospores for 10 minutes with gentle agitation (in order to keep particles and bacteria suspended). *E. coli* and *S. aureus* cells were tested at concentrations of $10^{11}$ cfu/ml and *B. thuringiensis* cells and endospores were utilized at a concentration of $10^8$ cfu/ml. After 10 minutes, the antimicrobial action of the powders was neutralized through the addition of 0.75 mL of sterile PBS containing 3 wt % $Na_2S_2O_3$ (a recognized chlorine neutralizing agent). An aliquot of the bacterial/titania suspension was removed and utilized to prepare serially diluted samples for plating. Experiments utilizing unhalogenated protamine/titania composite, Aeroxide P25 $TiO_2$ (commercially available from Evonik Ind. Inc.), and positive control samples (bacteria only, no protamine/titania composite) (at least 3 experiments for all samples) were conducted in parallel and utilized the same procedure as described for halogenated protamine-Cl/titania composite materials. Serially diluted samples were plated according to the drop plate method onto LB agar or spread onto nutrient broth agar plates. Plates were inverted and incubated for 16 hours at 37° C. and colonies were counted to determine the bactericidal or sporicidal activity of the materials. The antimicrobial activity of the tested materials is presented in Table 1. As detailed in Table 1, an at least about 4.7 Log reduction in the colony forming units of the bacterial cells or spores was obtained when the organisms were brought into contact with halogenated protamine-Cl/titania composite for 10 minutes. In contrast, unhalogenated protamine/titania composite and Aeroxide P25 $TiO_2$ induced less than 1 Log reduction in the colony forming units of the bacterial cells or spores.

TABLE 3

| | Log reduction in CFU (compared to positive control) | | | |
|---|---|---|---|---|
| Material tested | *B. thuringiensis* spores | *B. thuringiensis* cells | *S. aureus* cells | *E. coli* cells |
| halogenated protamine-Cl/ titania composite | 4.7 | >7 | >10 | >10 |
| unhalogenated protamine/ titania composite | 0.22 | 0.09 | 0.51 | 0.16 |
| Aeroxide P25 $TiO_2$ | 0.43 | 0.16 | 0.38 | 0.24 |

Example 5

In this example, the polypeptide poly-L-lysine was utilized both as an agent to induce the precipitation of an inorganic material (silica) and as a nitrogen source for chlorination. Poly-L-lysine hydrobromide salt, average molecular weight 47,900, as a white powder (commercially available from Sigma-Aldrich Co. (St. Louis, Mo.) was combined with 18.2 MΩ (resistivity of 18.2 megaohm-cm) water to produce a stock solution containing 10 mg poly-L-lysine/ml water. Silicic acid, the inorganic precursor, was prepared by hydrolyzing tetramethoxysilane in 1 mM hydrochloric acid to give a final concentration of 1 M silicic acid. Poly-L-lysine/silica composite materials were biomimetically synthesized through the preparation of a reaction mixture containing 50 mM, pH 7.5 sodium phosphate buffer, 1 mg/ml poly-L-lysine, and 100 mM silicic acid. The biomimetic silicification reaction was agitated for 10 minutes at 25° C. The poly-L-lysine contained within this solution condensed the silicic acid to form spherical poly-L-lysine/silica composite particles during the course of the reaction. The poly-L-lysine/silica composite particles were removed from the reaction solution by centrifugation at 5,000 rpm for 5 minutes, the excess reaction solution removed by decanting and the particles subsequently rinsed and re-suspended in 18.2 MΩ water. The poly-L-lysine/silica composite particles were further purified through 2 additional centrifugal collection and water rinsing steps.

FIG. 22 shows a SEM image of an unhalogenated poly-L-lysine/silica composite. SEM imaging revealed that the unhalogenated poly-L-lysine/silica composite possessed both hexagonal platelet and spherical morphologies. Following the final rinsing step, poly-L-lysine/silica powders were frozen in liquid nitrogen and dried for 16 hours in a freeze-drying unit.

FIG. 23 shows an EDS analysis of an unhalogenated poly-L-lysine/silica composite. EDS analysis indicated that the as-synthesized poly-L-lysine/silica material did not contain appreciable amounts of Cl.

FIG. 24 shows an EDS equipped SEM image of an unhalogenated poly-L-lysine/silica composite. Elemental mapping indicated that Si was, but Cl was not, associated with the unhalogenated poly-L-lysine/silica particles.

The poly-L-lysine contained within the synthesized poly-L-lysine/silica composite was then halogenated via a chemical reaction with a chlorine source (NaOCl), through the formation of covalent N—Cl bonds. In this example, the chlorination solution was composed of 10 vol % household bleach (commercially available from Clorox Company, Oakland, Calif.), 0.5 M NaCl, and was pH adjusted to pH 5.0 with 110 mM glacial acetic acid. In this example, 47 mg of poly-L-lysine/silica composite powder was combined with 7.5 mL of chlorination solution and agitated for 1 hour. The halogenated poly-L-lysine-Cl/silica composite particles were removed from the reaction solution by centrifugation at 5,000 rpm for 5 minutes, the excess reaction solution removed by decanting and the chlorinated particles subsequently rinsed and re-suspended in 18.2 MΩ water. The halogenated poly-L-lysine-Cl/silica composite particles were further purified through at least about 6 additional centrifugal collection and water rinsing steps. The complete removal of the chlorination reaction solution and free Cl from the halogenated poly-L-lysine-Cl/silica composite materials was verified through the testing of the decanted rinse water with potassium iodide/starch indicator papers (commercially available from Thermo Fisher Scientific Inc., Pittsburgh, Pa.) that detect low levels of chlorine. Following the final rinsing step, halogenated poly-L-lysine-Cl/silica composite powders were frozen in liquid nitrogen and dried for 16 hours in a freeze-drying unit. The active chlorine content of the halogenated poly-L-lysine-Cl/silica was determined by iodometric titration, utilizing a starch indicator end point to be 4.3 mmol Cl/g material.

Figure 25:
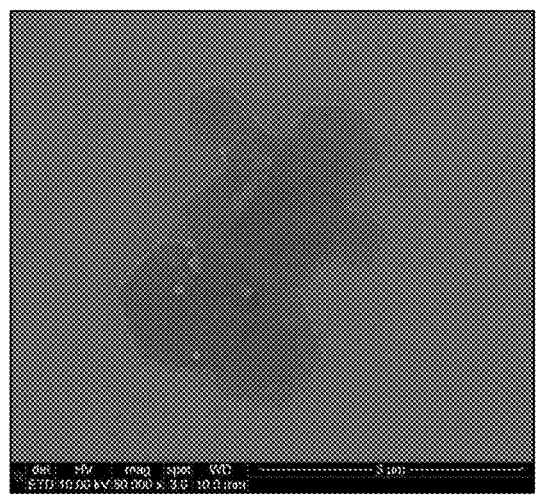
FIG. 25 shows a SEM image of a halogenated poly-L-lysine/silica composite.

FIG. 25 shows a SEM image of a halogenated poly-L-lysine/silica composite. SEM imaging revealed that the morphology of the poly-L-lysine-Cl/silica materials was unaffected by the halogenation process.

Figure 26:
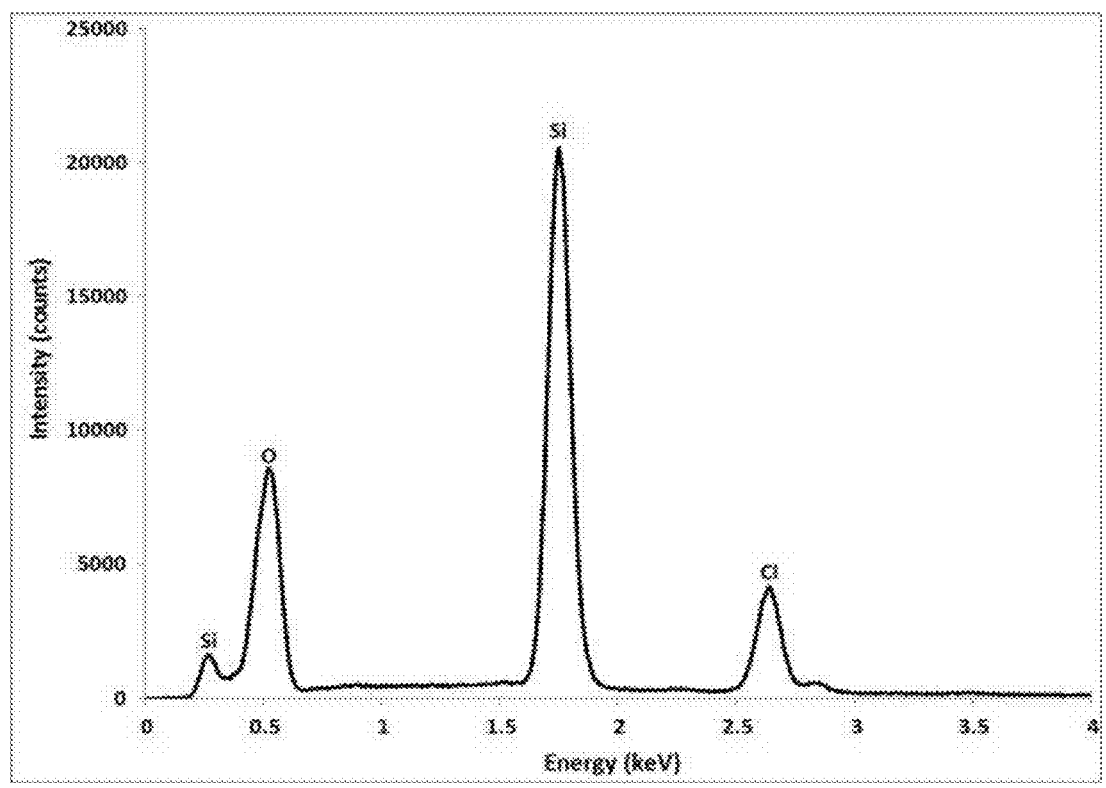
FIG. 26 shows an EDS graphical analysis of a halogenated poly-L-lysine/silica composite.

FIG. 26 shows an EDS analysis of a halogenated poly-L-lysine-Cl/silica composite. EDS analysis indicated that the halogenated poly-L-lysine-Cl/silica material contained appreciable amounts of Cl.

Figure 27:
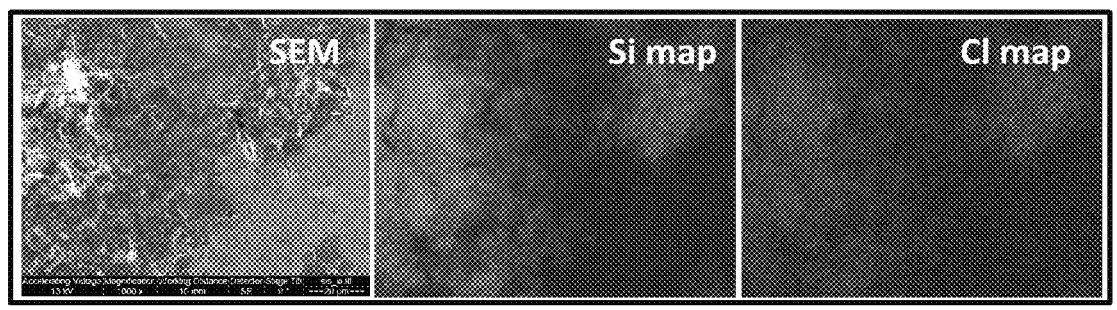
FIG. 27 shows an EDS equipped SEM image of a halogenated poly-L-lysine/silica composite.

FIG. 27 shows an EDS equipped SEM image of a halogenated poly-L-lysine-Cl/silica composite. Elemental mapping indicated that Cl was closely associated with Si and was consistent with the SEM observable morphology of the materials.

The antimicrobial activity of the prepared unhalogenated poly-L-lysine/silica and halogenated poly-L-lysine-Cl/silica composites was assessed in trials against vegetative *Escherichia coli* strain K12 (gram negative) cells. In this example, cultures of *E. coli* K12 were grown for 16 hours at 37° C. with shaking at 200 rpm in LB broth, Miller (commercially available from Amresco LLC., Solon, Ohio). Subsequent to culturing, the bacterial cells were collected by centrifugation at 5,000 rpm for 5 minutes, the growth broth was decanted and the cells rinsed and resuspended in an equivalent volume of sterile pH 7.4 sodium/potassium phosphate-buffered saline (PBS). The bacterial cells were collected by centrifugation and rinsed with sterile PBS 3 times. Following rinsing the vegetative cells were suspended in a desired volume of pH 7.4 PBS.

In this example, 0.05 g samples (at least 3 samples for each organism tested against) of halogenated poly-L-lysine-Cl/silica were exposed to 1 mL of sterile PBS containing vegetative bacterial cells for 1 hour with gentle agitation (in order to keep particles and bacteria suspended). *E. coli* cells were tested at concentrations of $10^6$ cfu/ml. After 1 hour, the antimicrobial action of the powders was neutralized through the addition of 0.75 mL of sterile PBS containing 3 wt % $Na_2S_2O_3$ (a recognized chlorine neutralizing agent). An aliquot of the bacterial/silica suspension was removed and utilized to prepare serially diluted samples for plating. Experiments utilizing unhalogenated poly-L-lysine/silica and positive control samples (bacteria only, no poly-L-lysine/silica composite) (at least 3 experiments for all samples) were conducted in parallel and utilized the same procedure as described for halogenated poly-L-lysine-Cl/silica composite materials. Serially diluted samples were plated according to the drop plate method onto LB agar plates. Plates were inverted and incubated for 16 hours at 37° C. and colonies were counted to determine the bactericidal activity of the materials. The results of this assay indicated that 100% of the bacterial cells were killed when brought into contact with halogenated poly-L-lysine-Cl/silica silica for 1 hour (i.e., at least about 6 Log reduction in colony forming units). In contrast, unhalogenated poly-L-lysine/silica composite induced only about a 0.06 Log reduction in the colony forming units of the *E. coli* cells.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

---

We claim:

1. A method of forming a biocidal halogenated organic/inorganic composite material comprising:
   providing at least one inorganic precursor chosen from a metal oxide, a metal hydroxide, a metal carbonate, a metal phosphate, a metal oxalate, a metal citrate, a metal halide, a metal sulfide, a metal selenide, or a metal telluride;
   providing at least one organic agent, wherein the organic agent comprises at least 20 wt % organic nitrogen-containing moieties and the organic agent is protamine;
   precipitating an organic/inorganic composite material by contacting the at least one inorganic precursor with the at least one organic agent; and halogenating the organic/inorganic composite material by contacting the organic/inorganic composite material with a halogen.

2. The method of claim 1, wherein the organic agent comprises at least 30 wt % nitrogen-containing moieties.

3. The method of claim 1, wherein the organic agent comprises at least 40 wt % nitrogen-containing moieties.

4. The method of claim 1, wherein the organic agent comprises at least 50 wt % nitrogen-containing moieties.

5. The method of claim 1, wherein the inorganic precursor comprises a ceramic, ceramic alloy, and/or ceramic mixtures.

6. The method of claim 1, wherein the inorganic precursor comprises the metal oxide.

7. The method of claim 1, wherein the inorganic precursor comprises silicic acid.

8. The method of claim 5, wherein the inorganic precursor comprises TiBALDH.

9. The method of claim 1, wherein the metal oxide is silica or titania, or combinations thereof.

10. The method of claim 1, wherein the halogen comprises one or more halogens selected from a group consisting of chlorine, bromine, and combinations thereof.

11. The method of claim 10, wherein the halogen comprises a solution comprising a chloride.

12. The method of claim 11, wherein the chloride is NaOCl.

13. The method of claim 1, further comprising rinsing the biocidal halogenated organic/inorganic composite material with water.

14. The method of claim 1, further comprising decontaminating a toxic chemical or biological agent susceptible to oxidation via halogen by contacting the toxic chemical or biological agent with the biocidal halogenated organic/inorganic composite material.

15. The method of claim 14, further comprising reloading the biocidal halogenated organic/inorganic composite material by further contacting the biocidal halogenated organic/inorganic composite material with the halogen.

16. The method of claim 1, further comprising applying the biocidal halogenated organic/inorganic composite material to a surface.

17. The method of claim 16, wherein the surface is a fibrous material.

18. The method of claim 17, wherein the fibrous material comprises silk, wool, or combinations thereof.

19. The method of claim 16, further comprising halogenating the organic/inorganic composite material after being applied to the surface.

20. A method of forming a biocidal halogenated organic/inorganic composite material comprising:
   providing at least one inorganic precursor chosen from a metal oxide, a metal hydroxide, a metal carbonate, a metal phosphate, a metal oxalate, a metal citrate, a metal halide, a metals sulfide, a metal selenide, or a metal telluride;
   providing at least one organic agent, wherein the organic agent comprises at least 20 wt % organic nitrogen-containing moieties, the organic agent is a peptide, and at least 25% of the amino acids of the peptide are arginine;
   precipitating an organic/inorganic composite material by contacting the at least one inorganic precursor with the at least one organic agent; and halogenating the organic/inorganic composite material by contacting the organic/inorganic composite material with a halogen.

21. The method of claim 20, wherein the organic agent comprises at least 30 wt % nitrogen-containing moieties.

22. The method of claim 20, wherein the organic agent comprises at least 40 wt % nitrogen-containing moieties.

23. The method of claim 20, wherein the organic agent comprises at least 50 wt % nitrogen-containing moieties.

24. The method of claim 20, wherein the inorganic precursor comprises a ceramic, ceramic alloy, and/or ceramic mixtures.

25. The method of claim 20, wherein the inorganic precursor comprises the metal oxide.

26. The method of claim 20, wherein the inorganic precursor comprises silicic acid.

27. The method of claim 20, wherein the inorganic precursor comprises TiBALDH.

28. The method of claim 20, wherein the metal oxide is silica or titania, or combinations thereof.

29. The method of claim 20, wherein the halogen comprises one or more halogens selected from a group consisting of chlorine, bromine, and combinations thereof.

30. The method of claim 20, wherein the halogen comprises a solution comprising chloride.

31. The method of claim 30, wherein the chloride is NaOCl.

32. The method of claim 20, further comprising rinsing the biocidal halogenated organic/inorganic composite material with water.

33. The method of claim 20, further comprising decontaminating a toxic chemical or biological agent susceptible to oxidation via halogen by contacting the toxic chemical or biological agent with the biocidal halogenated organic/inorganic composite material.

34. The method of claim 20, further comprising reloading the biocidal halogenated organic/inorganic composite material by further contacting the biocidal halogenated organic/inorganic composite material with the halogen.

35. The method of claim 20, further comprising applying the biocidal halogenated organic/inorganic composite material to a surface.

36. The method of claim 35, wherein the surface is a fibrous material.

37. The method of claim 36, wherein the fibrous material comprises silk, wool, or combinations thereof.

38. The method of claim 35, further comprising halogenating the organic/inorganic composite material after being applied to the surface.

* * * * *

UNITED STATES PATENT AND TRADEMARK OFFICE
CERTIFICATE OF CORRECTION

PATENT NO. : 9,028,807 B2  
APPLICATION NO. : 13/803448  
DATED : May 12, 2015  
INVENTOR(S) : Matthew B. Dickerson et al.

Page 1 of 1

It is certified that error appears in the above-identified patent and that said Letters Patent is hereby corrected as shown below:

In the Claims:

Col. 20, Claim 20, Line 4,
 "halide, a metals sulfide, a metal selenide, or a metal" should read
 --halide, a metal sulfide, a metal selenide, or a metal--; and Col. 20, Claim 31, Line 40,
 "NaOCI." should read
 --NaOCl.--.

Signed and Sealed this
Seventh Day of June, 2016

Michelle K. Lee
*Director of the United States Patent and Trademark Office*